(12) United States Patent
Stock et al.

(10) Patent No.: US 9,777,542 B2
(45) Date of Patent: Oct. 3, 2017

(54) AUTOMATED DRILLING FLUID ANALYZER

(75) Inventors: Tore Stock, Kleppe (NO); Egil Ronaes, Hundvag (NO); Thomas Hilton, Kirkland, WA (US)

(73) Assignee: SCHLUMBERGER NORGE AS, Hafrsfjord (NO)

( * ) Notice: Subject to any disclaimer, the term of this patent is extended or adjusted under 35 U.S.C. 154(b) by 1065 days.

(21) Appl. No.: 13/578,332

(22) PCT Filed: Feb. 10, 2011

(86) PCT No.: PCT/US2011/024356
§ 371 (c)(1),
(2), (4) Date: Jun. 6, 2013

(87) PCT Pub. No.: WO2011/100435
PCT Pub. Date: Aug. 18, 2011

(65) Prior Publication Data
US 2015/0316527 A1    Nov. 5, 2015

Related U.S. Application Data

(60) Provisional application No. 61/303,207, filed on Feb. 10, 2010, provisional application No. 61/308,076, (Continued)

(51) Int. Cl.
*G01N 11/10* (2006.01)
*E21B 21/01* (2006.01)
(Continued)

(52) U.S. Cl.
CPC .............. *E21B 21/01* (2013.01); *E21B 47/00* (2013.01); *G01N 11/10* (2013.01); *G01N 21/64* (2013.01);
(Continued)

(58) Field of Classification Search
CPC .......... E21B 21/01; E21B 47/00; E21B 21/08; E21B 49/005; G01N 23/223; G01N 21/64;
(Continued)

(56) References Cited

U.S. PATENT DOCUMENTS 4,484,468 A    11/1984   Gau et al.
5,361,631 A *  11/1994   Covington ............ E21B 49/005
                                                  73/152.24
(Continued)

FOREIGN PATENT DOCUMENTS

CN    2095419 U    2/1992
CN    2488064 Y    4/2002
(Continued)

OTHER PUBLICATIONS

International Search Report and Written Opinion for International Application No. PCT/US2011/024356 dated Dec. 28, 2011.
(Continued)

*Primary Examiner* — John Fitzgerald
*Assistant Examiner* — Truong Phan
(74) *Attorney, Agent, or Firm* — Sara M. Hinkley

(57) ABSTRACT

An automatic drilling fluid property analyzer including a housing having an inlet and an outlet; at least one valve disposed proximate the inlet and configured to open and close to provide a sample of fluid into the housing; an electronic control module configured to send a signal to the at least one valve; a probe assembly operatively coupled to the electronic control module, the probe assembly including an electrode probe having two electrodes and a probe gap therebetween; a viscometer sleeve disposed in the housing; a bob disposed in the sleeve, wherein an annulus is formed between the viscometer sleeve and the bob, and wherein at least one of the viscometer sleeve and the bob is configured (Continued)

to rotate, a motor operatively coupled to at least one of the viscometer sleeve and the bob; and a torque measuring device operatively coupled to the viscometer sleeve and the bob.

15 Claims, 29 Drawing Sheets

Related U.S. Application Data filed on Feb. 25, 2010, provisional application No. 61/308,137, filed on Feb. 25, 2010, provisional application No. 61/370,541, filed on Aug. 4, 2010.

(51) Int. Cl.
*E21B 47/00* (2012.01)
*G01N 27/92* (2006.01)
*G01N 21/64* (2006.01)
*G01N 33/28* (2006.01)
*G01N 23/223* (2006.01)
*G01N 11/14* (2006.01)

(52) U.S. Cl.
CPC ........... *G01N 23/223* (2013.01); *G01N 27/92* (2013.01); *G01N 33/2823* (2013.01); *G01N 11/14* (2013.01)

(58) Field of Classification Search
CPC .... G01N 27/92; G01N 11/10; G01N 33/2823; G01N 23/2204; G01N 27/023; G01N 27/07; G01N 27/20; G01N 21/359; G01N 11/14; G01N 11/16; G01N 24/081; G01N 2223/076; G01N 23/04; G01R 1/067; G01R 1/07314; G01R 27/02; G01R 19/0092; G01R 27/16; G01R 33/50; G06Q 10/06; G06F 19/70; G01V 3/32; G01V 5/0016; G01V 5/0008
USPC ............ 378/47, 57; 324/724, 722, 713, 303; 702/30; 73/152.19, 54.23
See application file for complete search history.

(56) References Cited

U.S. PATENT DOCUMENTS

| | | | |
|---|---|---|---|
| 5,519,214 A | 5/1996 | Houwen et al. | |
| 6,233,307 B1* | 5/2001 | Golenhofen | G01N 23/207 378/44 |
| 2001/0013247 A1* | 8/2001 | Wilson | G01N 33/2858 73/54.01 |
| 2001/0042400 A1 | 11/2001 | Boyle et al. | |
| 2004/0104355 A1 | 6/2004 | DiFoggio et al. | |
| 2004/0234029 A1* | 11/2004 | De Lange | G01N 23/22 378/70 |
| 2005/0129580 A1* | 6/2005 | Swinehart | B01F 5/0475 422/400 |
| 2007/0087927 A1* | 4/2007 | Scott | E21B 21/062 494/7 |
| 2008/0283294 A1 | 11/2008 | Colquhoun | |
| 2009/0087911 A1 | 4/2009 | Ramos | |
| 2009/0096440 A1 | 4/2009 | Murphy et al. | |
| 2009/0141862 A1 | 6/2009 | Dunham et al. | |
| 2010/0004890 A1* | 1/2010 | Tonmukayakul | G01N 11/14 702/113 |
| 2010/0158704 A1* | 6/2010 | Charlton | F04B 53/1032 417/53 |
| 2010/0283492 A1* | 11/2010 | Growcock | G01N 33/2823 324/724 |
| 2011/0048377 A1* | 3/2011 | Song | F02M 37/0029 123/445 |

FOREIGN PATENT DOCUMENTS

| | | |
|---|---|---|
| CN | 2786615 Y | 6/2006 |
| CN | 2816796 Y | 9/2006 |
| CN | 2938073 U | 8/2007 |
| CN | 201181282 Y | 1/2009 |
| CN | 101551347 A1 | 10/2009 |
| CN | 101629916 A | 1/2010 |
| EP | 1926886 B1 | 10/2009 |
| GB | 2417564 A | 3/2006 |
| SU | 655933 A1 | 4/1979 |
| WO | 00/54025 A1 | 9/2000 |
| WO | 2009/055672 A1 | 4/2009 |
| WO | 2009062041 A2 | 5/2009 |

OTHER PUBLICATIONS

Second Office Action for Chinese Patent Application No. 201180018419.4 dated Oct. 24, 2014 (19 pages).
Search Report to Chinese Patent Application No. 201180018419.4 dated Jan. 6, 2014 (27 pages).
Office action for the equivalent Eurasian patent application 201290760 dated Mar. 13, 2014.
Office acttion for the equivalent Mexican patent application MX/a/2012/009163 dated May 15, 2014.
Third office action for the equivalent Chinese patent application 201180018419.4 dated May 11, 2015.
Partial search report for the equivalent European patent application 11742797.1 dated Jun. 17, 2015.
Extended search report for the equivalent European patent application 11742797.1 dated Oct. 2, 2015.
Extended search report for the equivalent European patent application 15184306.7 dated Dec. 18, 2015.
Office action for the equivalent Eurasian patent application 201400741 dated Mar. 9, 2016.
Office action for the equivalent Eurasian patent application 201290760 dated May 11, 2016.
Fourth office action for the equivalent Chinese patent application 201180018419.4 dated Jul. 26, 2016.
Office action for the equivalent Indonesian patent application 00201203218 dated Oct. 31, 2016.
Office action for the equivalent Malaysian patent application PI2012700544 dated Jan. 31, 2017.
Examination Report for the equivalent Australian patent application 2011215835 dated Dec. 22, 2014.
Examination Report for the equivalent Australian patent application 2016231571 dated May 1, 2017.

* cited by examiner

SETUP - PAGE1

| NUMBER OF PROFILES: | 0 | TEMPERATURE HOLD TIME: | 0 |
|---|---|---|---|
| NUMBER OF RAMPS: | 0 | DELAY BETWEEN RAMPS: | 0 |
| NUMBER OF WIPES: | 0 | CYCLE DELAY (MINUTES): | 0 |
| MUD IN DURATION (SEC): | 0 | PRESSURE SET POINT (BAR): | 0 |
| COOL DOWN DURATION (SEC): | 0 | BASE IN DURATION (SEC): | 0 |

BASE SOAK DURATION (SEC): 0

SETUP - PAGE2

| TEMPERATURE SETPOINT 1 (C): | 0 | TEMPERATURE SETPOINT 6 (C): | 0 |
|---|---|---|---|
| TEMPERATURE SETPOINT 2 (C): | 0 | TEMPERATURE SETPOINT 7 (C): | 0 |
| TEMPERATURE SETPOINT 3 (C): | 0 | TEMPERATURE SETPOINT 8 (C): | 0 |
| TEMPERATURE SETPOINT 4 (C): | 0 | TEMPERATURE SETPOINT 9 (C): | 0 |
| TEMPERATURE SETPOINT 5 (C): | 0 | TEMPERATURE SETPOINT 10 (C): | 0 |

← MAIN

*FIG. 12*

SYSTEM STATUS - PAGE1

| | |
|---|---|
| WIPER NOT PARKED | WIPER MOTOR RUNNING |
| DOOR OPENED | WIPER CLOCKWISE |
| MUD SOLENOID ENERGIZED | PROBE RELAY ENERGIZED |
| BASE SOLENOID ENERGIZED | 500V RELAY ENERGIZED |
| WATER SOLENIOD ENERGIZED | 1900V RELAY ENERGIZED |
| AIR SOLENIOD ENERGIZED | |

SYSTEM STATUS - PAGE2

| | |
|---|---|
| VOLTAGE READING | 0 |
| CURRENT READING | 0 |
| TEMPERATURE READING | 0 |
| PRESSURE READING | 0 |

AUTOMATIC TEST SETUP

| MAIN | | |
|---|---|---|
| NUMBER OF PROFILES ## | COOL DOWN DURATION(SEC) ## | BASE SOAK DURATION(SEC) ## |
| NUMBER OF RAMPS ## | BASE IN DURATION(SEC) ## | |
| NUMBER OF WIPES ## | | |
| MUD IN DURATION ##SEC | TEMPERATURE SETPOINT 1 ## | TEMPERATURE SETPOINT 6 ## |
| TEMPERATURE HOLD TIME ##SEC | TEMPERATURE SETPOINT 2 ## | TEMPERATURE SETPOINT 7 ## |
| DELAY BETWEEN RAMPS ##SEC | TEMPERATURE SETPOINT 3 ## | TEMPERATURE SETPOINT 8 ## |
| TO TEST CYCLE (MINUTES) ## | TEMPERATURE SETPOINT 4 ## | TEMPERATURE SETPOINT 9 ## |
| PRESSURE SET POINT ##PSI | TEMPERATURE SETPOINT 5 ## | TEMPERATURE SETPOINT 10 ## |

*FIG. 19*

| MAIN | TESTING DATA DISPLY | |
|---|---|---|
| | TYPE = #, ##########, ## ##, ####VAC, ###uA, ##C | TYPE 1 - AUTOMATIC TEST |
| | TYPE = #, ##########, ## ##, ####VAC, ###uA, ##C | TYPE 2 - 500V CALIBRATION |
| | TYPE = #, ##########, ## ##, ####VAC, ###uA, ##C | TYPE 3 - 1900V CALIBRATION |
| | TYPE = #, ##########, ## ##, ####VAC, ###uA, ##C | TYPE 4 - MANUAL AIR TEST |
| | TYPE = #, ##########, ## ##, ####VAC, ###uA, ##C | TYPE 5 - AUTOMATIC WATER TEST |
| | TYPE = #, ##########, ## ##, ####VAC, ###uA, ##C | |
| | TYPE = #, ##########, ## ##, ####VAC, ###uA, ##C | |
| | TYPE = #, ##########, ## ##, ####VAC, ###uA, ##C | |
| | TYPE = #, ##########, ## ##, ####VAC, ###uA, ##C | |
| | TYPE = #, ##########, ## ##, ####VAC, ###uA, ##C | |
| | TYPE = #, ##########, ## ##, ####VAC, ###uA, ##C | |
| | TYPE = #, ##########, ## ##, ####VAC, ###uA, ##C | |
| | TYPE = #, ##########, ## ##, ####VAC, ###uA, ##C | |
| | TYPE = #, ##########, ## ##, ####VAC, ###uA, ##C | |

*FIG. 20*

AUTOMATED DRILLING FLUID ANALYZER

BACKGROUND OF INVENTION

Field of the Invention

Embodiments disclosed herein relate to an automated meter to measure the electrical stability of drilling fluids. More specifically, embodiments disclosed herein relate to a drilling fluid analyzer for determining viscosity, gel strength, and or electric stability. More specifically still, embodiments disclosed herein relate to methods and systems for determining viscosity, gel strength, and or electric stability of drilling fluids that include automation and remote control.

Background Art

When drilling oil and/or gas wells, oil-based drilling fluids are often used to cool the drill bit, remove rock chips, and control subsurface fluids. Various properties of this fluid can be measured to compute useful results. For example, the electrical stability of drilling fluid is a property that is typically measured using an electrical stability (ES) test. The ES test is typically a manual test that is performed by a mud engineer or an equivalent technician. Conventionally, when performing an ES test, a probe that includes circular flat electrodes of diameter ⅛ inch, spaced 1/16 inch between faces, is inserted into the drilling fluid. Drilling fluid, which contains non-aqueous fluid, water (or other polar liquid), clays, and other materials, fills the gap between the two electrodes of the test probe. Wires run from the probe to a signal generator and measurement meter, which ramps the voltage between the electrodes until components of the fluid align to form a short-circuiting bridge. When the short circuit occurs, the current between the electrodes immediately spikes. Specifically, an AC voltage of 340 Hz is ramped at 150 V s$^{-1}$ until a peak current (approximately 61 µA) occurs. At this stage, the peak voltage, known as the breakdown voltage ($V_{BD}$) is captured by the meter. 61 µA is the current at which the breakdown voltage occurs for the above-described geometry of the probe. The breakdown voltage is the voltage at which the drilling fluid's electrical properties become electric field-dependent and is the voltage at which the electrical conductivity of the drilling fluid becomes non-ohmic. Thus, the breakdown voltage is related to the emulsion stability and is then used to compute the emulsion stability and other properties of the drilling fluid.

Typically, to measure the electrical stability of drilling fluid using the above manual probe method, the drilling fluid and associated fluid is kept static, as movement and shifts in the fluids of the drilling fluid may cause the measurements taken by the electrodes and recorded by the meter to be skewed. In addition, when using the manual probe method described above, the electrodes and the gap between electrodes of the probe are manually cleaned after each measurement sampling.

In addition to measuring electrical stability, drilling rig operators may perform tests to determine viscosity. Typically, such measurements were performed with instruments such as a Marsh funnel viscometer. Marsh funnels are manually operated measurement devices that provide a drilling operator a general idea as to the viscosity of a particular fluid. In use, the funnel is held vertically and the end tube closed by covering the outlet with a finger. Fluid to be measured is then poured into the funnel until the fluid reaches a line indicating about 1.5 liters. To take the measurement, the finger is removed from the outlet and a stopclock is started. The fluid exits the funnel and the time to remove one quart of fluid from the funnel is recorded. With a known volume and a discharge time, the viscosity may be calculated.

While such measurement techniques give operators a general idea as to the viscosity, due to the manual implementation, the results may not always be accurate. Additionally, the viscosity of the fluid downhole is not truly known, because the fluid cannot be heated or measured under pressure.

In addition to electrical stability and viscosity, the gel strength of the fluid can also be determined. Gel strength is the measure of a fluid's ability to hold particles in suspension, and the gel strength is measure using a concentric cylinder viscometer. Gel strength is also measured manually and the results analyzed when adjusting the properties of the drilling fluid.

Accordingly, there exists a need for an automated method for measuring the electrical stability, viscosity, and/or gel strength of drilling fluid. Additionally, there exists a need for improved methods for sampling drilling fluid for appropriate measurements and cleaning of the electrodes of the probe used to measure the breakdown voltage of the drilling fluid.

SUMMARY OF INVENTION

In one aspect, the embodiments disclosed herein relate to an automated electrical stability meter for measuring electrical stability of a sample of fluid, the meter including a housing having an inlet and an outlet; at least one valve disposed proximate the inlet and configured to open and close to provide a sample of fluid into the housing; an electronic control module configured to send a signal to the at least one valve; and a probe assembly operatively coupled to the electronic control module, the probe assembly including an electrode probe having two electrodes and a probe gap therebetween.

In another aspect, embodiments disclosed herein relate to an automated viscometer including a housing having an inlet and an outlet; a viscometer sleeve disposed in the housing; a bob disposed in the sleeve, wherein an annulus is formed between the viscometer sleeve and the bob, and wherein at least one of the viscometer sleeve and the bob is configured to rotate, a motor operatively coupled to at least one of the viscometer sleeve and the bob; and a torque measuring device operatively coupled to the viscometer sleeve and the bob.

In another aspect, embodiments disclosed herein relate to an automatic drilling fluid property analyzer including a housing having an inlet and an outlet; at least one solenoid valve disposed proximate the inlet and configured to open and close to provide a sample of fluid into the housing; an electronic control module configured to send a signal to the at least one solenoid valve; a probe assembly operatively coupled to the electronic control module, the probe assembly including an electrode probe having two electrodes and a probe gap therebetween; a viscometer sleeve disposed in the housing; a bob disposed in the sleeve, wherein an annulus is formed between the viscometer sleeve and the bob, and wherein at least one of the viscometer sleeve and the bob is configured to rotate, a motor operatively coupled to at least one of the viscometer sleeve and the bob; and a torque measuring device operatively coupled to the viscometer sleeve and the bob.

In another aspect, embodiments disclosed herein relate to computer-assisted method for automated drilling fluid property analysis, the method including a software application executing on a processer, the software application including instructions for transferring a drilling fluid from an active fluid system; filling a sample cell with the drilling fluid; directing the fluid through an electric probe, wherein the electric probe comprises a probe gap between two electrodes; applying a voltage across the probe gap; determining an electric stability of the drilling fluid based at least in part on the applied voltage; transferring the drilling fluid from the sample cell to the active fluid system; and cleaning the sample cell.

In another aspect, embodiments disclosed herein relate to A computer-assisted method for automated drilling fluid property analysis, the method including a software application executing on a processer, the software application including instructions for transferring a drilling fluid from an active fluid system; filling a sample cell with the drilling fluid; directing the drilling fluid in the sample cell into an annulus between a sleeve and a bob of a viscometer; rotating at least one of the sleeve and the bob; determining at least one of a viscosity and a gel strength of the drilling fluid based on the rotation of the at least one of the sleeve and the bob; transferring the drilling fluid from the sample cell to the active fluid system; and cleaning the sample cell.

In another aspect, embodiments disclosed herein relate to computer-assisted method for controlling an automatic drilling fluid property analyzer, the method including a software application executing on a processer, the software application including instructions for sending a control signal from a remote location to the drilling fluid property analyzer at a drilling location; verifying the control signal was received by the drilling fluid analyzer; receiving data from the drilling fluid analyzer; processing the data received from the drilling fluid analyzer; and determining at least one of a viscosity, gel strength, and electrical stability of a drilling fluid in the drilling fluid property analyzer.

Other aspects and advantages of the invention will be apparent from the following description and the appended claims.

BRIEF DESCRIPTION OF DRAWINGS

FIGS. 8-21 are graphical displays according to embodiments of the present disclosure.

DETAILED DESCRIPTION

In one aspect, embodiments disclosed herein relate to an automated meter to measure emulsion stability and rheological properties of drilling and completion fluids. More specifically, embodiments disclosed herein relate to autonomous analysis of drilling and completion fluids that may be performed or analyzed remote from the rig or testing site.

Embodiments disclosed herein relate to a method and apparatus for automating the measurement of properties of invert emulsion oil-based or synthetic-based fluids (i.e., drilling fluids and/or completion fluids) and water based fluids. Although the disclosure herein may reference drilling fluid, one of ordinary skill in the art will appreciate that other types of fluids (e.g., completion fluids) may also be tested with the method and apparatus disclosed herein.

Figure 1:
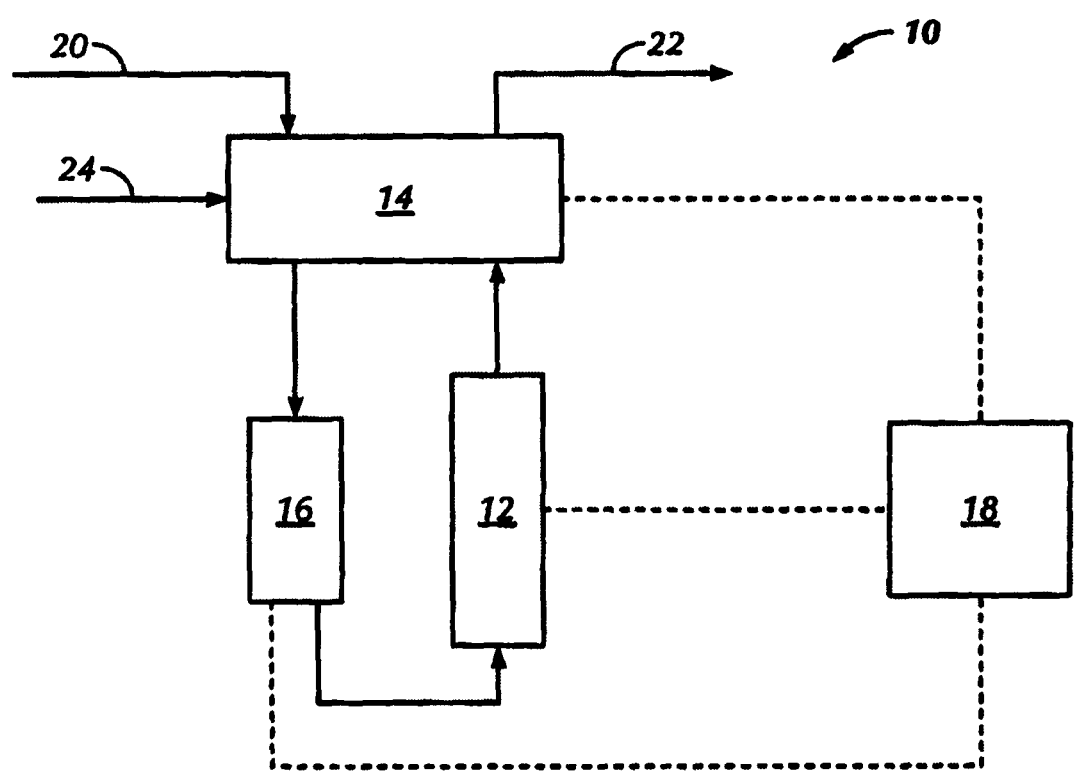
FIG. 1 is a schematic of a general automated fluid analyzer in accordance with embodiments disclosed herein.

Referring to FIG. 1, a general schematic of an automated fluid property analyzer 10 in accordance with embodiments disclosed herein is shown. The automated fluid property analyzer 10 is placed in line with an active fluid system and configured to obtain a sample of fluid from the system for analyzing. As shown, the automated fluid property analyzer 10 includes a sample cell 12, a valve block 14, and a pump 16. Although the valve block 14 is illustrated as a single unit, one of ordinary skill in the art will appreciate that valve block 14 may include one or more valves arranged as necessary to provide fluid flow in and out of the sample cell 12. An electronic control module 18 is operatively connected to the sample cell 12, valve block 14, and pump 16, as designated by the phantom lines. Generally, a fluid is pumped by pump 16 through inlet 20 of valve block 14 into sample cell 12. The pump 16 may be, for example, a pneumatic pump or a positive displacement pump. The fluid may be tested in sample cell 12 and/or cycled through the sample cell and out through outlet 22 in valve block 14. The valve block 14 may also include a cleaning fluid inlet 24 through which a cleaning fluid may be pumped into the sample cell 12 for cleaning the sample cell 12 between tests of the fluid. One of ordinary skill in the art will appreciate that various fluids may be used for cleaning the sample cell 12. For example, the cleaning fluid may be mineral oil, diesel, or water and may include various chemical additives, such as surfactants and/or acid.

As discussed in greater detail below, the sample cell 12 may include a housing (not shown) configured to contain a desired volume of fluid for sampling and analyzing. One of ordinary skill in the art will appreciate that the volume of the housing may vary based on the type of fluid to be sampled, size constraints of the location at which the sampling is to be performed, and the types of analysis to be performed. In some embodiments, the volume of the sample cell housing may be in a range between 0.25 L and 1.0 L. In some embodiments, the volume of the sample cell is 0.5 L. The sample cell 12 may include devices or components configured to determine at least one of an electrical stability, a gel strength, and a viscosity of the fluid sampled, as discussed below. For example, in one embodiment, the sample cell may include an automated electrical stability meter, an automated viscometer, or a combination of both.

The electronic control module 18 includes electronics configured to send and/or receive signals between the components of the sample cell 12, the valve block 14, and pump 16 to automate the sampling and analysis process. The electronic control module 18 may send periodic signals to the valve block 14 and a component for determining an electrical stability of a sample fluid in the sample cell 12, thereby initializing a measurement reading. The electronic control module 18 may be configured to control the timing between measurement readings/data acquisition. Those skilled in the art will appreciate that the frequency of measurement readings may be determined by factors other than timing. For example, drilling fluid may be sampled and measured based on the quantity of drilling fluid that is driven through the sample cell 12. Alternatively, drilling fluid may be sampled and measured on-demand and/or in real-time.

In one or more embodiments, configuration files stored on a USB flash drive (not shown), or other type of computer readable medium or storage device, are provided to the electronic control module 18 via a USB connector (not shown). Those skilled in the art will appreciate that other types of connectors and storage devices may also be employed. For example, an SD card and corresponding SD connector may be used to store and load configuration files. Alternatively, a hard drive, floppy disk drive, internal memory, or a CD may also be used. The configuration files may include probe waveform definitions, calibration data, and automated and manual process definitions for the electronic control module 18.

Figure 2:
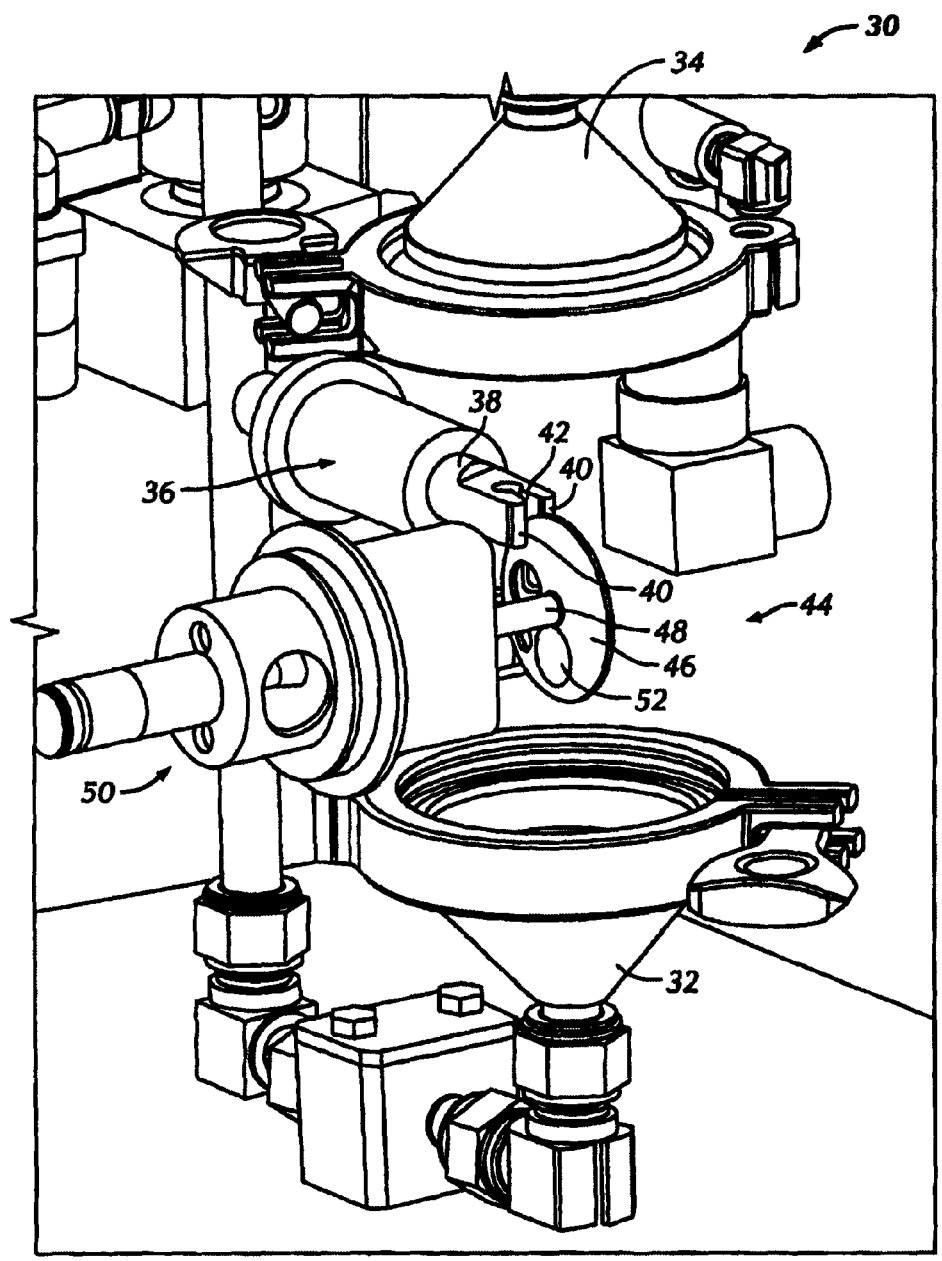
FIG. 2 is a partial perspective view of an automated electrical stability meter in accordance with embodiments disclosed herein.

Referring now to FIG. 2, an automated electrical stability meter 30 for measuring electrical stability of a sample of fluid is shown in accordance with embodiments disclosed herein. The automated electrical stability meter 30 includes a housing (not shown) configured to contain a volume of fluid to be analyzed. The sample fluid enters the housing through an inlet 32 and exits the housing through an outlet 34. A pump (not shown) is configured to pump the sample fluid in and out of the housing when signaled from the electronic control module (not shown).

A probe assembly 36 is disposed in the housing (not shown) and operatively coupled to the electronic control module (not shown). The probe assembly 36 includes an electrode probe 38 for measuring the electrical stability and other properties of the drilling fluid. The electrode probe 38 is a fork-shaped probe with two electrodes 40 on each tong-like piece. Between the two electrodes 40 is a probe gap 42. When fluid fills the volume of the housing, the fluid is directed through the probe gap 42 of the probe assembly 36. A voltage is applied across the probe gap to determine an electric stability of the drilling fluid based at least in part on the applied voltage. A series of measurements, i.e., a testing sequence, may be taken with the same fluid sample in the housing.

The electrical stability meter 30 may also include a cleaning mechanism 44 configured to clean the probe gap 42 between the two electrodes 40. The cleaning mechanism 44 is configured to remove any residue from the surface of the electrodes 40 or stuck in the probe gap 42 to ensure proper test results of subsequent fluid samples. As shown in FIG. 2, cleaning mechanism 44 may include a rotating disc 46 coupled to a shaft 48. The shaft 48 is coupled to a motor 50. Motor 50 is coupled to an outer surface of the housing (not shown), and the shaft 48 extends into the housing proximate the probe assembly 36. When the motor 50 receives a signal from the electronic control module (not shown), the motor 50 rotates the shaft 48 and, therefore, the disc 46. The width of the disc 46 is approximately equal to the width of the probe gap 42 (i.e., the distance between the two electrodes 40). Therefore, as the disc 46 is rotated between the electrodes 40, the disc 46 removes any remaining residue from the probe gap 42 and the electrodes 40. The electronic control module (not shown) may operate the cleaning mechanism 44 between sampling and testing sequences. Cleaning of the probe assembly 36 may be performed at predetermined time intervals or may be individually initiated by the electronic control module (not shown).

The disc 46 may be formed from any material known in the art capable of cleaning a surface. In one embodiment, the disc 46 is formed from a flexible material so as to prevent damage to the electrodes 40. Disc 46 may be formed from polyethylene, for example ultra high molecular weight polyethylene (UHMW), or polytetrafluoroethylene (PTFE). As shown, the disc 46 includes a cutout or opening 52 extending through the width of the disc 46. Once cleaning of the probe assembly 36 is completed, rotation of the disc 46 is stopped such that the opening 52 is in alignment with the probe gap 42. Thus, analysis of a sample of fluid is to be performed, the opening 52 of the disc 46 is positioned between the electrodes 40 in the probe gap 42 so as to provide a maximum volume of sample fluid between the electrodes 40 for measurement of the electrical properties of the fluid.

A position indicator (not shown) may be coupled to the motor 50 or the rotating disc 46. The position indicator (not shown) is operatively coupled to the electronic control module (not shown) and configured to send a signal representative of the location of the rotating disc 46 and the opening 52. The signal representative of the location of the rotating disc 46 may be compared to predetermined values for locations of the disc 46 with respect to the probe assembly 36 for sampling and testing sequences or cleaning sequences to ensure that the opening 52 is properly aligned with the probe assembly 36. While the cleaning mechanism 44 as described may include a rotating disc 46, one of ordinary skill in the art will appreciate that other cleaning mechanisms may be used without departing from the scope of embodiments disclosed herein. For example, a wiper blade may be rotated into and out of the probe gap 42, an actuated squeegee may wipe the surfaces of the electrodes 40, or jets may be installed proximate the electrodes to blast residue off of the electrodes 40 with fluid, such as water, base oil, or air.

In some embodiments, the automated electrical stability meter 30 may include an agitator (not shown). In one embodiment, the agitator may include a one or more turbine blades coupled to the cleaning mechanism 44. For example, one or more turbine blades may be coupled to the shaft 48 and/or the rotating disc 46. Thus, as the rotating disc 46 is operated, the turbine blades (not shown) of the agitator (not shown) also rotate and mix the fluid contained within the housing. Rotation of the agitator (not shown) stirs or mixes the fluid contained in the housing and reduces or prevents settling of particulates or separation of liquids in the fluid. The electronic control module (not shown) may operate the agitator (not shown) between sampling and testing sequences. Agitation of the fluid in the housing may be performed at predetermined time intervals or may be individually initiated by the electronic control module (not shown).

A thermal jacket (not shown) is disposed around the housing (not shown) of the automated electrical stability meter 30. The thermal jacket is configured to heat the sampled fluid contained within the housing (not shown). In one embodiment, the thermal jacket includes an electrical circuit configured to supply an alternating current to heat the fluid contained in the housing (not shown). In another embodiment, the thermal jacked includes an electrical circuit configured to supply a direct current to heat the fluid contained in the housing (not shown). The electronic control module (not shown) may be used to control the electrical circuit in the thermal jacket and, therefore, heating of the sample fluid.

To cool the fluid contained in the housing, a water jacked may be disposed around the housing (not shown) of the automated electrical stability meter 30. For example, cooling loop 56 (FIG. 3) may be run along a portion of the housing or around the circumference of the housing (not shown). In this embodiment, a water supply line 64 (FIG. 3) may be connected to a loop of tubing encircling or placed adjacent the housing (not shown) of the automated electrical stability meter 30. A valve may be actuated by, for example, the electronic control module to provide a flow of fluid having a temperature less than the sample fluid to the cooling loop. Heat from the sample fluid is transferred to fluid flowing through the cooling loop 56 (FIG. 3), thereby cooling the sample fluid. The cooling fluid may be, for example, water, sea water, or any other fluid known in the art. The cooling loop 56 may allow for a more rapid cooling of the sample fluid, thereby decreasing the time between tests. As the time between tests may be decreased, more frequent samples of the fluid may be obtained, thereby informing a drilling engineer as to changes in electrical stability and gel strength.

In other embodiments, a Peltier device (not shown) may be coupled to the housing and used to cool and/or heat the fluid contained in the housing. A Peltier device uses the Peltier effect to create heat flux across the device. The Peltier device may be coupled to a DC voltage generator. The resultant temperature of the sample fluid may be determined by the amount of current provided to the Peltier device.

A temperature sensor (not shown) may be disposed in the housing of the automated electrical stability meter 30. The temperature sensor is operatively coupled to the electronic control module (not shown) and is configured to sense and transmit data representative of the temperature of the sample fluid. The electronic control module may be configured to continuously monitor the temperature of the sample fluid, to monitor the temperature of the sample fluid at timed intervals, to monitor the temperature of the sample fluid before and/or after each testing sequence, or to monitor the temperature of the sample fluid at manually initiated times. Based on readings of the temperature sensor (not shown) and a predetermined desired temperature input value, the electronic control module (not shown) may initiate heating or cooling of the sample fluid, as discussed above.

Figure 2B:
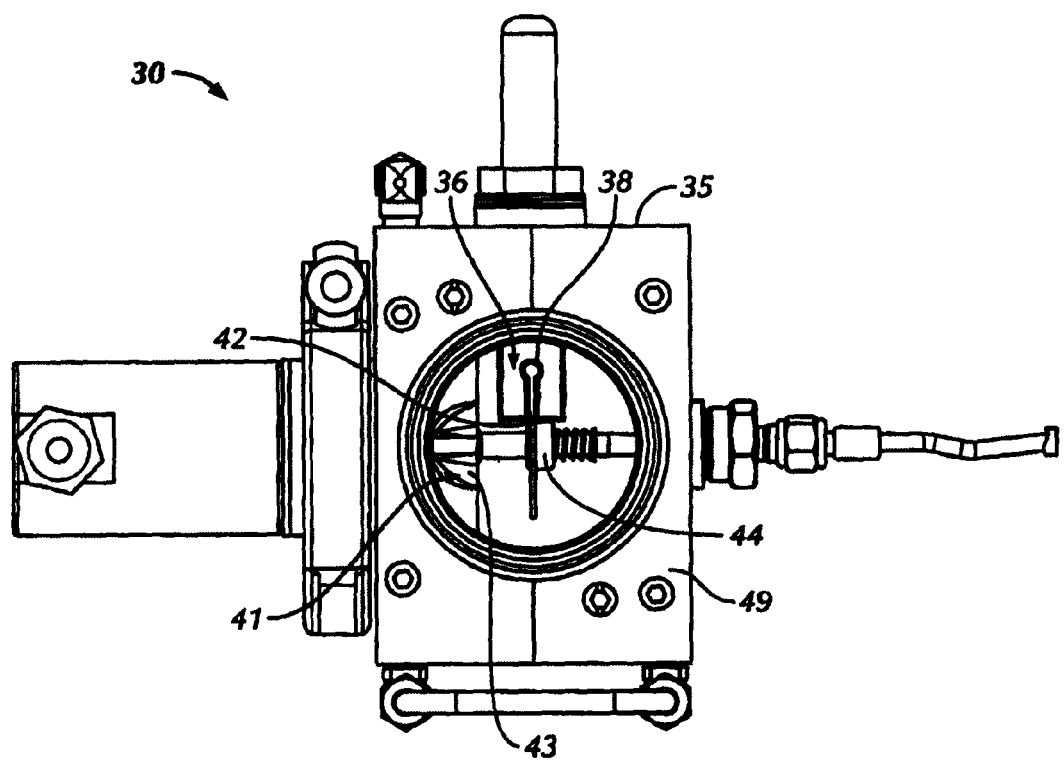
FIG. 2B shows a top view of an automated electrical stability meter in accordance with embodiments disclosed herein.

Referring to FIG. 2B, a top view of the electrical stability meter 30 of FIG. 2, according to embodiments of the present disclosure is shown. In this embodiment, electrical stability meter 30 includes a probe assembly 36 disposed in a housing 35. An electrode probe 38 is configured to measure the electrical stability, as well as other properties of a sample drilling fluid. Between electrodes (not shown) of electrode probe 38, a probe gap 42 is formed. During operation, a sample drilling fluid is provided in the probe gap 42, a voltage is applied across the probe gap 42 such that an electrical stability of the sample drilling fluid may be determined. A cleaning mechanism 44, such as a wiper blade, may be configured to rotate into probe gap 42, thereby allowing the probe gap 42 to be cleaned between testing cycles.

Electrical stability meter 30 also includes an agitator 41 that is configured to rotate. Agitator 41 includes one or more blades 43 that may be rotated in order to mix fluid within the housing 35. The mixing of fluid within housing 35 prevent solids particles from settling out or otherwise separating from the mixing during and between testing cycles. In certain embodiments, housing 35 may also includes a heating/cooling jacket 49. The heating/cooling jacket 49 may thereby heat and subsequently cool sample drilling fluids, thereby allowing the fluid to be tested according to downhole conditions. Additionally, the jacket 49 may allow the sample drilling fluid to be cooled more rapidly between test cycles, thereby decreasing the time between tests.

Figure 3:
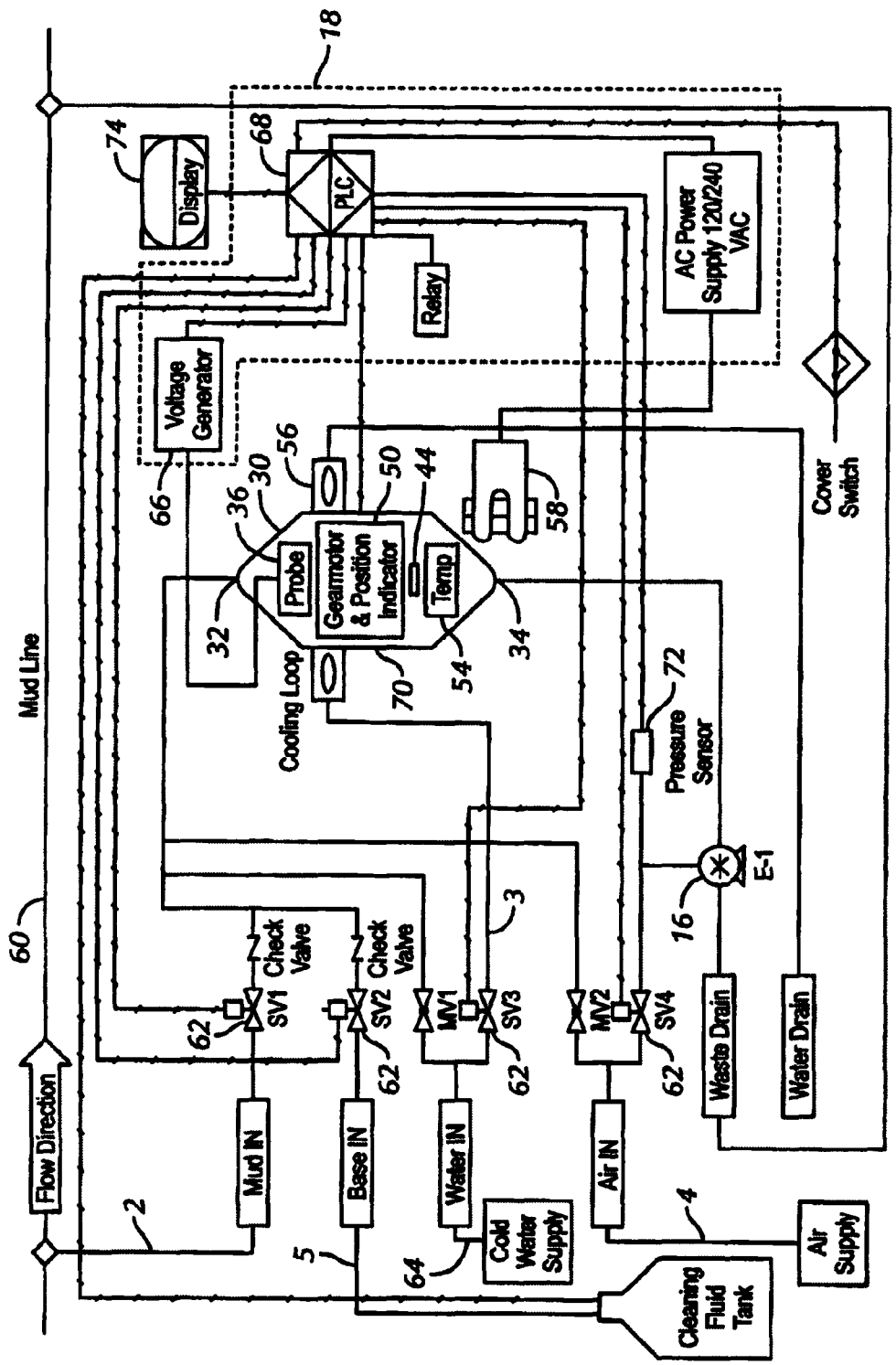
FIG. 3 is a process and instrumentation diagram of an automated electrical stability meter in accordance with embodiments disclosed herein.

Referring now to FIG. 3, a process and instrumentation diagram of the closed system automated electrical stability meter 30 is shown. As shown, an automated electrical stability meter 30 is placed in line with an active fluid system 60. A plurality of valves 62 control flow of fluids in and out of the automated electrical stability meter 30. In one embodiment, at least one valve 62 is a solenoid valve, while in other embodiments, valve 62 may include check valves or combinations of solenoid and check valves. In certain embodiments, rather than a solenoid valve, other types of actuated valves may be used. In certain embodiments, solenoid valves having large passageways are coupled to the inlet 32 and outlet 34 of the automated electrical stability meter 30. Such solenoid valves may be used to prevent a build up of residue, particles, or debris from settling out of the fluid transported therethrough and blocking the valve. Such valves are commercially available from ASCO® (Florham Park, N.J.). The solenoid valves may be also be positioned so as to prevent material from settling into areas of the valve that may prevent proper actuation of the valve.

Figure 3A:
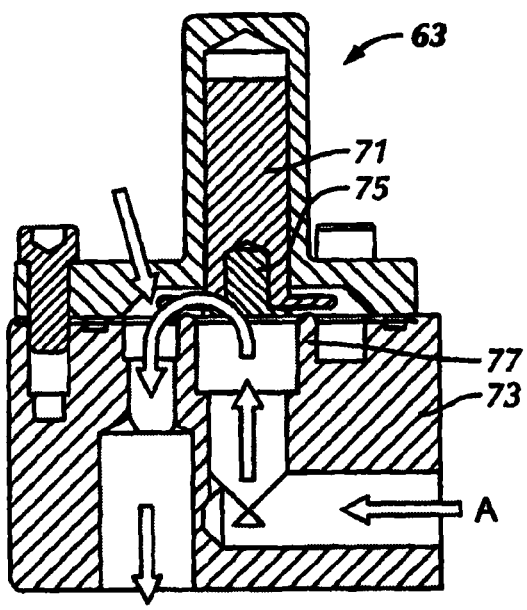
FIGS. 3A and 3B are cross-sectional views of a check valve according to embodiments of the present disclosure.
Figure 3B:
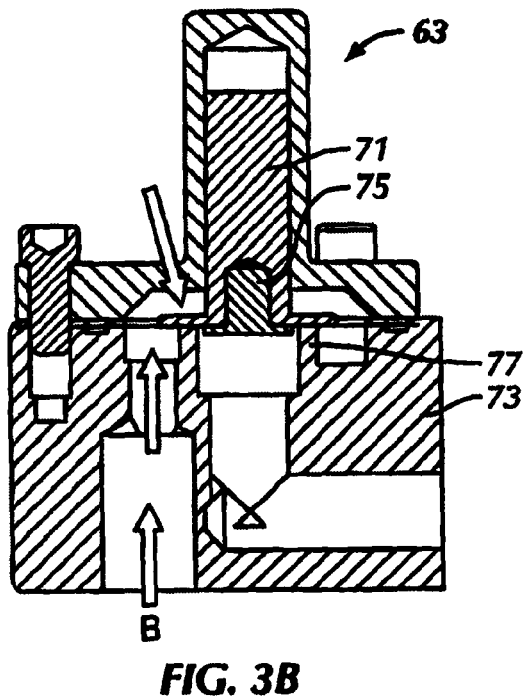
Figure 3C:
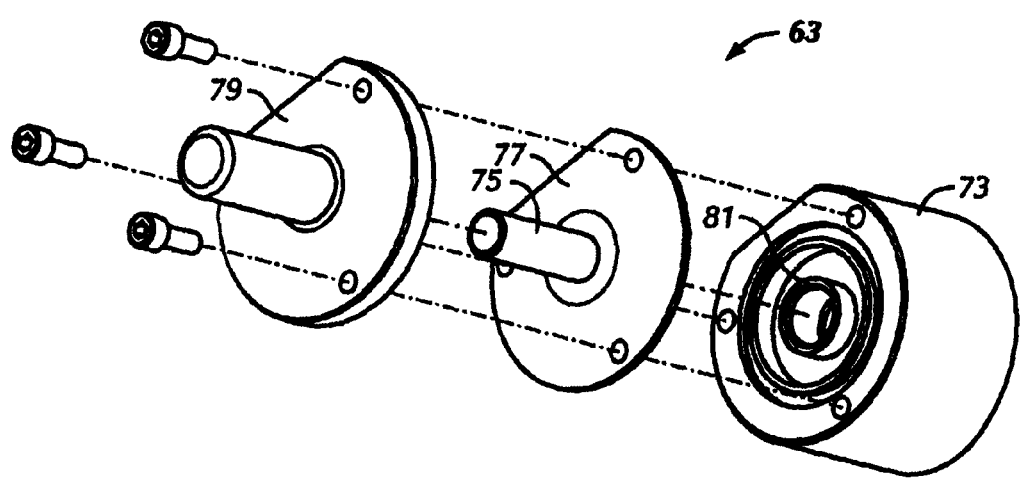
FIG. 3C is an exploded view of a check valve according to embodiments of the present disclosure.

Referring briefly to FIGS. 3A and 3B, a specific type of valve 62 according to embodiments of the present disclosure is shown. In FIG. 3A, a check valve 63 is shown. The check valve 63 includes a plunger 71, a valve body 73, and a plunger assembly 75 including an elastomer material 77. During a fill stage of the testing (FIG. 3A), during low pressure conditions, the fluid is flowing along path A, thereby moving the plunger 71 into an open position and allowing fluid to flow into the electrical stability meter. During a high pressure condition, such as during a back flow, the fluid is flowing in direction B (of FIG. 3B), causing the plunger 71 to close and seal check valve 63. Such a one-way check valve may be less prone to failure from liquids or slurries that are highly viscous or contain particulate matter. Referring briefly to FIG. 3C, an exploded view of check valve 63 is shown. As illustrated, check valve 63 includes a valve body 73, a plunder assembly 75 having an elastomer material 77, and a plunger guide 79. The elastomer material 77 is configured to seal against sealing surface 81 of valve body 73, and is configured to remain constrained within plunger guide 79. Those of ordinary skill in the art will appreciate that in certain embodiments, a check valve 63 may be used along or in combination with other types of valves, such as the solenoid valves described above.

Referring back to FIG. 3, s shown, a valve 62 is actuated on a fluid inlet line 2 to sample fluid from the active fluid system 60. The electronic control module 18 includes, for example, a programmable logic controller 68 or a micro processor and a voltage generator 66. The electronic control module 18 is configured to send a signal to at least one of the valves 62 to open or close. The sample fluid is directed through the inlet 32 of the automated electrical stability meter 30. A temperature sensor 54 operatively coupled to the electronic control module 18 is disposed in the housing 70 of the automated electrical stability meter 30. If the temperature sensed by the temperature sensor 54 is above or below a predetermined temperature value, the electronic control module 18 sends a signal to the thermal jacket 58 or the cooling loop 56 to heat or cool, respectively, the sample fluid.

Specifically, if the temperature of the sample fluid needs to be raised, the electronic control module 18 sends a signal to generate a current in the thermal jacket 58. The electrical current in the thermal jacket heats the sample fluid until the predetermined temperature is reached. Similarly, if the temperature of the sample fluid needs to be lowered, the electronic control module 18 sends a signal to a valve 62 disposed on the cooling loop line 3 to circulate water (or other fluids) from the water supply line 64 around the housing 70 of the automated electrical stability meter 30, thereby cooling the sample fluid. The temperature sensor 54 may continuously monitor the temperature of the fluid during heating or cooling periods of the sample fluid.

A pressure sensor 72 may be operatively coupled to the housing 70 and to the electronic control module 18. If the pressure sensed by the pressure sensor 72 in the closed system automated electrical stability meter 30 is below or above a predetermined pressure value, the electronic control module 18 signals the valve 62 on an air supply line 4 to open or close to increase or decrease, respectively, the pressure inside the housing 70.

The probe assembly 36 disposed in the automated electrical stability meter 30 is actuated by the electronic control module 18 and a voltage is supplied by the voltage generator 66 to the probe electrodes (not independently illustrated). The voltage generator may supply a ramped voltage to the probe assembly 36, as set by control circuitry in the electronic control module 18. In one embodiment, the voltage generator may supply 0 to 2,000 volts to the probe assembly 36.

The standard API electrical stability test specifies a 340 Hz sinusoidal AC signal that ramps from 0-2000 volts at 150 volts per second. The procedure (i.e., software) stored in a configuration file is used to determine when to drive a particular waveform signal to the probe assembly 36. In one or more embodiments, the waveform(s) are stored as separate files and may not be part of the configuration file. The API standard ES reading is the peak voltage at which the current reaches 61 µA. However, the configuration file may also provide the ECM with signals that are based on a non-linear voltage ramp and/or other types of ramp rates. Those skilled in the art will appreciate that the specifications of the electrical stability test may be changed by programming different waveforms onto the configured file that is fed to the electronic control module. Thus, the threshold current may be a value higher or lower than 61 µA.

The electronic control module 18 controls actuation of the cleaning mechanism 44. At predetermined intervals or as needed, the motor 50 is actuated by the electronic control module 18, thereby rotating the wiper or rotating disc (not shown) into the probe gap (not shown) of the probe assembly 36. The position indicator (not shown) sends signals back to the electronic control module 18 indicating the rotational position of the disc or the relative position of the cleaning mechanism 44 with respect to the probe gap. The motor 50 may also be signaled by the electronic control module 18 to actuate the agitator (not shown). The agitator may be run to ensure thorough mixing of the fluid and reduce and/or prevent settling of material within the housing.

After the testing sequence is completed, the electronic control module 18 signals the outlet 34 to open and initiate the pump 16 to pull the sample fluid from the housing 70 of the automated electrical stability meter 30 and return the sample fluid to the active fluid system 60. An additional sampling and testing sequence may then be initiated or a cleaning sequence may be initiated. To implement a cleaning sequence, electronic control module 18 sends a signal to the cleaning mechanism 44, as discussed above, and sends a signal to a valve 62 on a cleaning fluid line 5 to open the valve 62 and transfer cleaning fluid to the housing 70. The cleaning mechanism 44 is operated within the housing 70 while the cleaning fluid is flushed through the housing. The agitator (not shown) may also be run to enhance cleaning of the housing 70 and probe assembly 36. Cleaning fluid may be drained through the outlet 34 and discarded.

Figure 4:
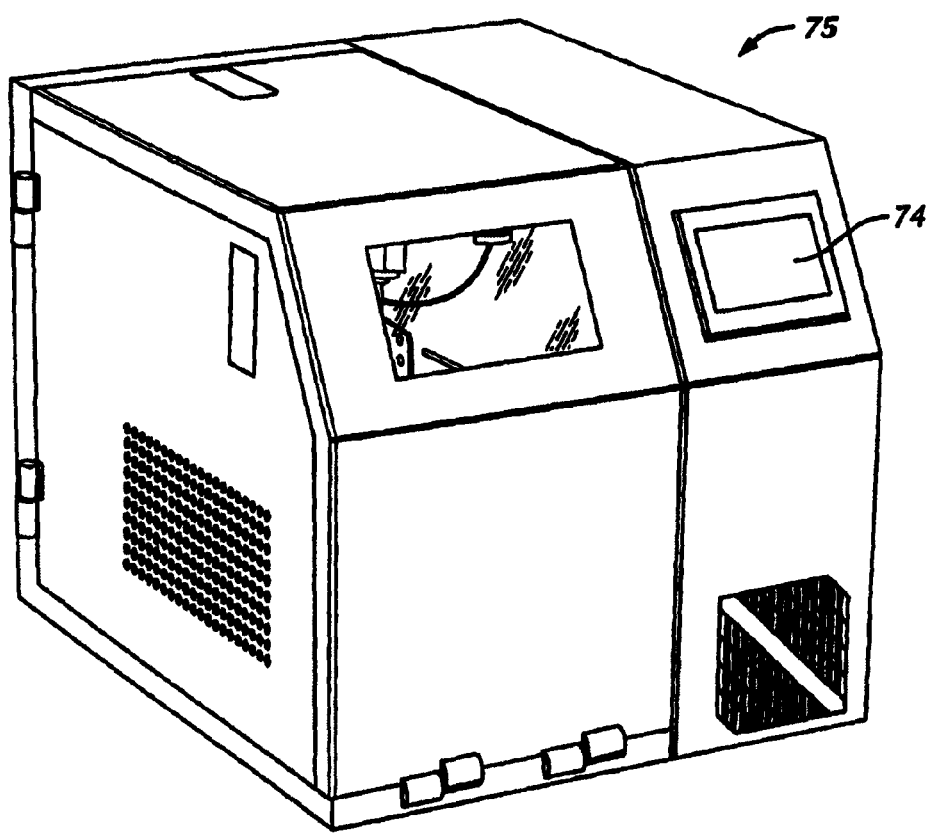
FIG. 4 is a perspective view of a shell housing of an electrical stability meter in accordance with embodiments disclosed herein.

Referring to FIGS. 3 and 4 together, the automated electrical stability meter 30, including the housing 70, electronic control module 18, valves 62, and various supply lines and drain lines may be disposed within in a shell housing 75. The shell housing 75 encloses all of the main components of the automated electrical stability meter 30. The shell housing 75 may include a plurality of ports or connections for connecting fluid lines, for example, the active fluid system line, water lines, drain lines, etc. to the housing 70 of the automated electrical stability meter 30. A display 74 mounted to the shell housing 75 is configured to display information representative of the results of signals sent and received by the electronic control module 18. For example, the display 74 may display electrical stability of the sample fluid, temperature of the sample fluid, pressure within the housing 70, etc.

Figure 5:
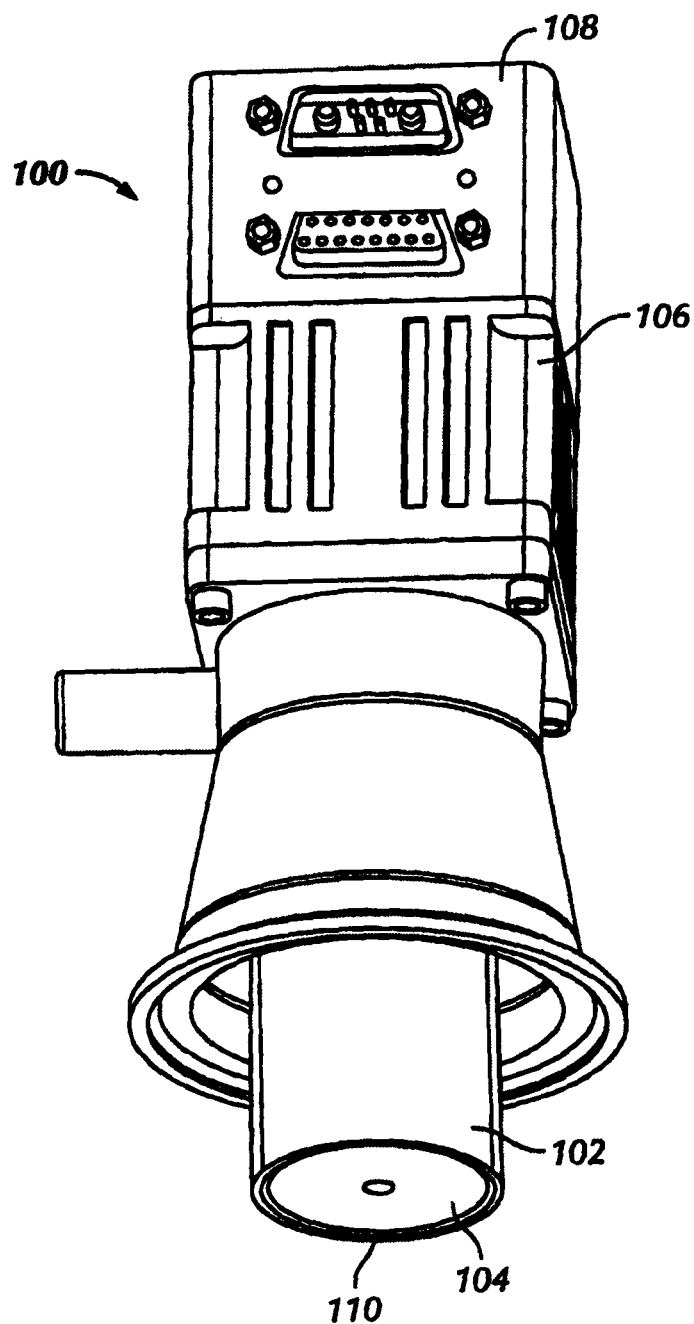
FIG. 5 is a partial perspective view of an automatic drilling fluid property analyzer in accordance with embodiments disclosed herein.

Referring now to FIG. 5, an automated viscometer 100 for measuring gel strength and/or viscosity of a sample of fluid is shown in accordance with embodiments disclosed herein. The automated electrical stability meter 30 includes a housing (not shown) configured to contain a volume of fluid to be analyzed. Similar to the automated electrical stability meter discussed above, the sample fluid enters the housing through an inlet (not shown) and exits the housing through an outlet (not shown). A pump (not shown) is configured to pump the sample fluid in and out of the housing when signaled from an electronic control module (not shown).

The automated viscometer 100 includes a viscometer sleeve 102 disposed in the housing (not shown), a bob 104 disposed in the sleeve 102, a motor 106 operatively coupled to at least one of the viscometer sleeve 102 and the bob 104, and a torque measuring device 108 operatively coupled to the viscometer sleeve 102 and/or the bob 104. In the embodiment shown, the bob 104 is suspended by a torsion wire 131 (FIG. 6B) from the torque measuring device 108 and the sleeve 102 is rotated by the motor 106. An annulus 110 is formed between the viscometer sleeve 102 and the bob 104. After a sample fluid is transferred from the active drilling fluid system into the housing, the fluid is directed to the annulus 110 between the viscometer sleeve 102 and the bob 104. Depending on the configuration of the automated viscometer 100, either the viscometer sleeve 102 or bob 104 is rotated at a specific speed by the motor 106. The specific speed determines the shear rate of the fluid inside the annulus 110. The torque exerted on bob 104 or viscometer sleeve 102, as determined by the torque measuring device 108, is recorded, and the data is either stored or sent to a remote computer system for processing, as described below. For example, the torque measuring device 108 may measure the amount of twist of the torsion wire 131 caused by the drag rotation of the bob 104. Said another way, torque measuring device 108 may measure the torque caused by movement of the torsion wire 131. Based on the torque detected, the viscosity and gel strength of the fluid may be determined.

As described in detail above with respect to the automated electrical stability meter 30 (FIG. 2), the electronic control module 18 (FIG. 1) may similarly control the automated viscometer 100. The electronic control module 18 (FIG. 1) may send signals to solenoid valves (not shown) to open and close flow lines for directing a sample fluid from an active fluid system into the housing (not shown) of the automated viscometer 100. Once the housing is filled with a sample fluid, the electronic control module 18 (FIG. 1) may send a signal to the motor 106 to run/spin the bob 104 of sleeve 102. The torque measuring device 108 may determine an applied torque based on specified speed of rotation and the drag rotation the sample fluid in the annulus 110 creates on the non-rotating bob 104 or sleeve 102. The data collected by the torque measuring device 108 may be sent to the electronic control module 18 (FIG. 1) for further processing. Once the sample fluid has completed the testing sequence, the electronic control module 18 sends a signal to a valve (not shown) and a pump (not shown) to transfer the sample fluid back to the active fluid system (not shown).

In one embodiment, a magnetic coupling (not shown) may be disposed between the bob 104 and the torque measuring device 108. Because the torque measured by the torque measuring device 108 is typically very low, seal drag between the bob 104 and the torque measuring device 108 should be reduced or eliminated. The magnetic coupling (not shown) reduces or eliminates seal drag between the bob 104 and the torque measuring device 108 for more accurate measurement of the torque on the bob 104.

Similar to the automated electrical stability meter 30 (FIG. 2), temperature and pressure sensors (not shown) may be disposed within the housing of the automated viscometer 100 to determine and monitor the temperature and pressure of the sample fluid contained therein. Additionally, the electronic control module 18 (FIG. 1) may actuate a thermal jacket, a cooling loop, or initiating pressurization or depressurization of the housing based on a comparison of the determined temperature and pressure and predetermined temperature and pressure values. The closed system automated viscometer 100 provides maintenance of the temperature and pressure of the fluid within the housing, which may improve the accuracy of the rheological properties of the fluid measured.

Figure 6A:
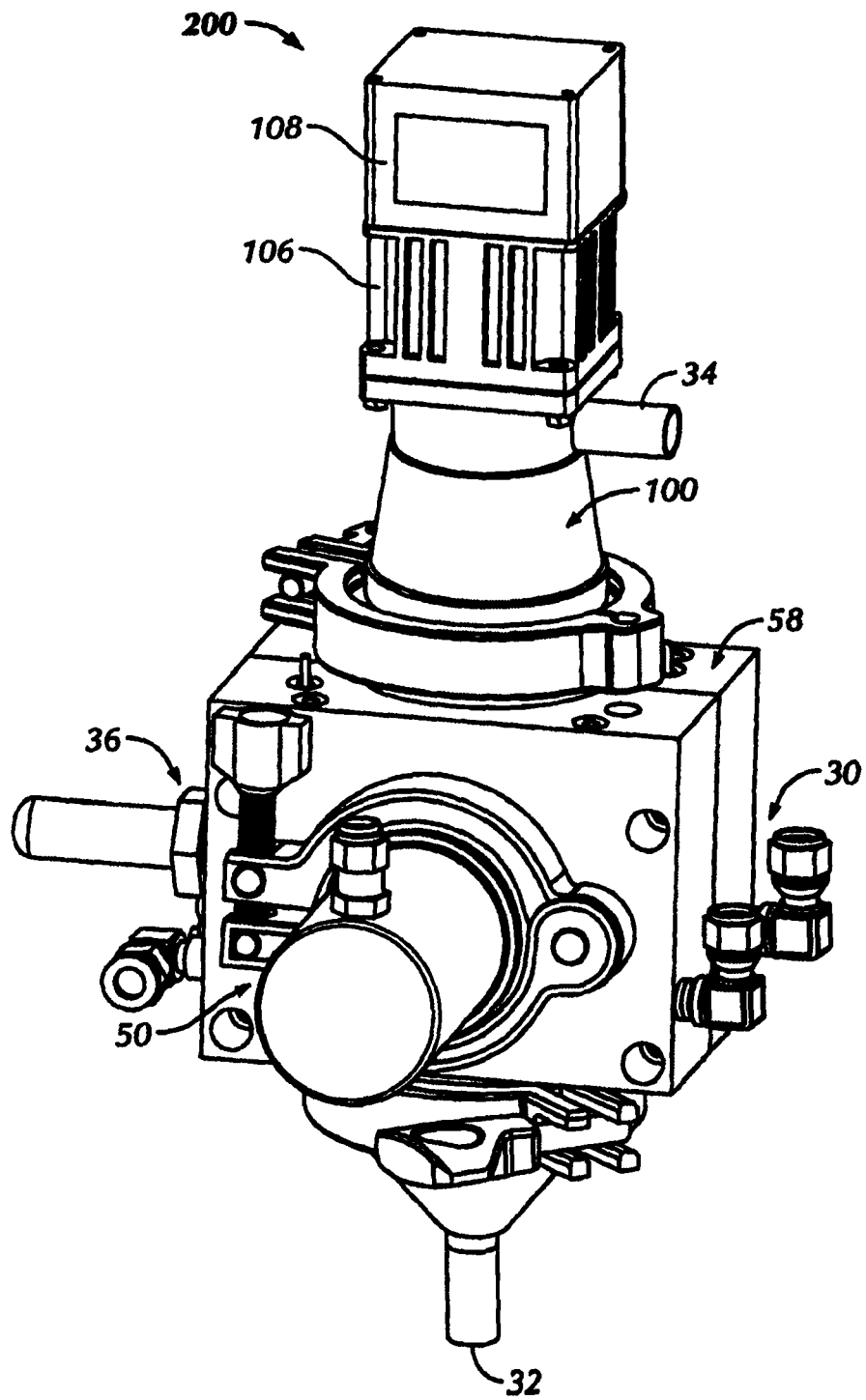
FIGS. 6A and 6B are perspective and cross-sectional views, respectively, of an automated viscometer in accordance with embodiments disclosed herein.
Figure 6B:
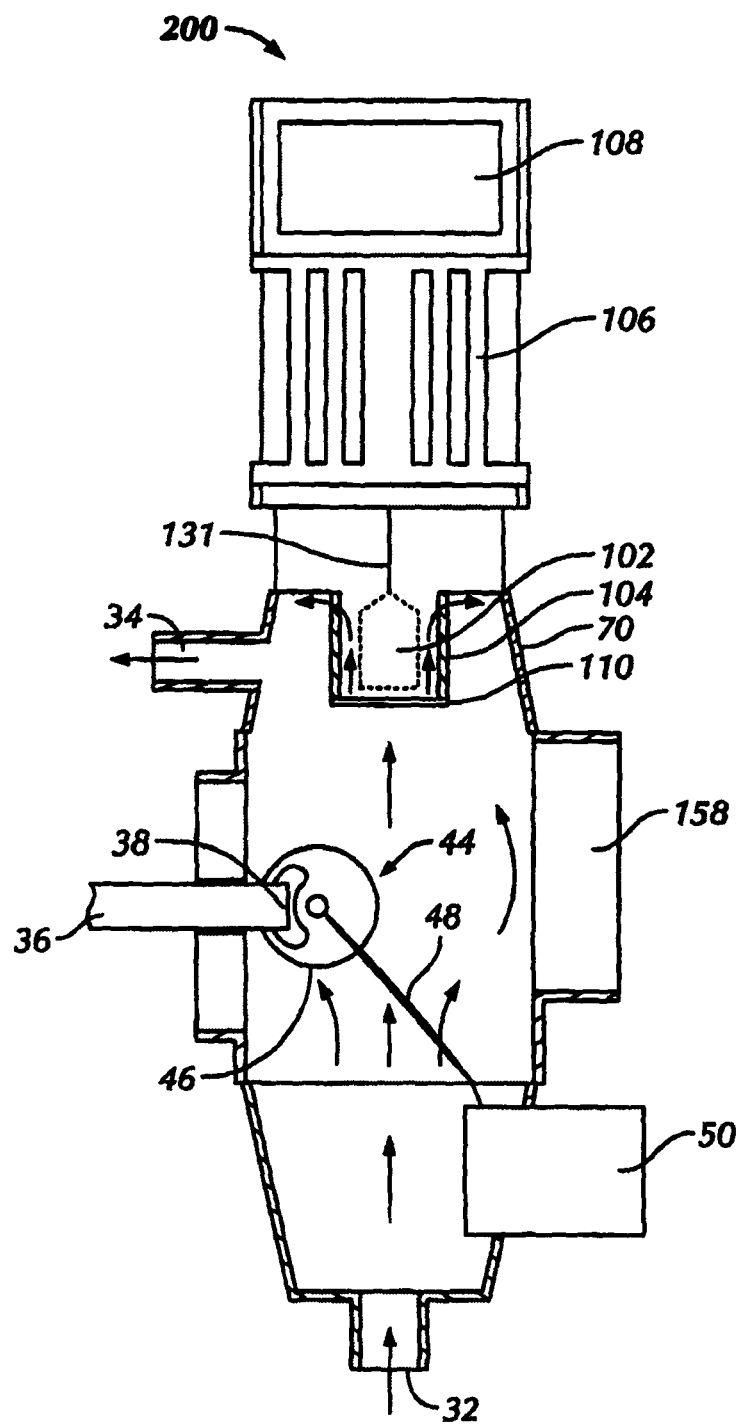

Referring now to FIGS. 6A and 6B, an automatic drilling fluid property analyzer 200 in accordance with embodiments disclosed herein is shown. The automatic drilling fluid property analyzer 200 includes an automated electrical stability meter 30 and an automated viscometer 100. As shown, the automatic drilling fluid analyzer 200 includes a housing 70 having an inlet 32 and an outlet 34. At least one solenoid valve (not shown) is disposed proximate at least one of the inlet 32 and the outlet 34 and configured to open and close to provide a sample of fluid from an active fluid system into the housing 70.

A temperature sensor (not shown) may be disposed inside the housing 70 and configured to determine a temperature of the fluid contained therein. A thermal jacket 58 encases at least a portion of the housing 70 and is configured to heat the sample fluid if the temperature sensor senses a temperature below a predetermined value or it otherwise actuated by the electronic control module 18 (FIG. 1). A cooling loop (not shown) or a water jacket (not shown) may also enclose at least a portion of the housing 70. The cooling loop is configured to cool the sample fluid in the housing 70 if the temperature sensor senses a temperature above a predetermined value.

A pressure sensor (not shown) may be operatively coupled to the housing 70 and configured to determine a pressure inside the housing. If the pressure sensor senses a pressure below a predetermined pressure value, air or fluid may be added to the housing 70 through a valve-controlled flow line (not shown) to increase the pressure. If the pressure sensor senses a pressure above the predetermined pressure value, a valve may be opened to relieve the pressure within the housing 70.

A probe assembly 36 is coupled to the housing 70 for measuring electrical stability of the sample fluid in the housing 70. The probe assembly 36 includes an electrode probe 38 having two electrodes (not shown) extending into a volume of the housing 70. A cleaning mechanism 44 is disposed in the housing 70 and configured to move into engagement with a probe gap (not shown) between the electrodes of the electrode probe 38. In the embodiment shown, the cleaning mechanism 44 includes a rotating disc 46 coupled to a shaft 48 rotated by a motor 50. Motor 50 is coupled to an outer surface of housing 70 and is configured to rotate the cleaning mechanism 44 and/or an agitator (not shown). A position indicator (not shown) may be coupled to the motor 50 or the cleaning mechanism 44 and configured to detect a relative position of the cleaning mechanism 44 with respect to the probe assembly 36.

The viscometer sleeve 104 and bob 102 of the automated viscometer 100 are disposed in the housing 70. As discussed above with respect to the automated viscometer 100, a motor 106 is operatively coupled to at least one of the viscometer sleeve 102 and the bob 104, and a torque measuring device 108 is operatively coupled to the viscometer sleeve 102 and/or the bob 104. In the embodiment shown, the bob 104 is suspended by a torsion wire 131 from the torque measuring device 108 and the sleeve 102 is rotated by the motor 106. An annulus 110 is formed between the viscometer sleeve 102 and the bob 104. Depending on the configuration, either the viscometer sleeve 102 or bob 104 is rotated at a specific speed by the motor 106. The specific speed determines the shear rate of the fluid inside the annulus 110. The torque exerted on bob 104 or viscometer sleeve 102, as determined by the torque measuring device 108, is recorded, and the data is either stored or sent to a remote computer system for processing, as described below. For example, the torque measuring device 108 may measure the amount of twist of the torsion wire 131 caused by the drag rotation of the bob 104. Based on the torque detected, the viscosity and gel strength of the fluid may be determined.

Figure 7A:
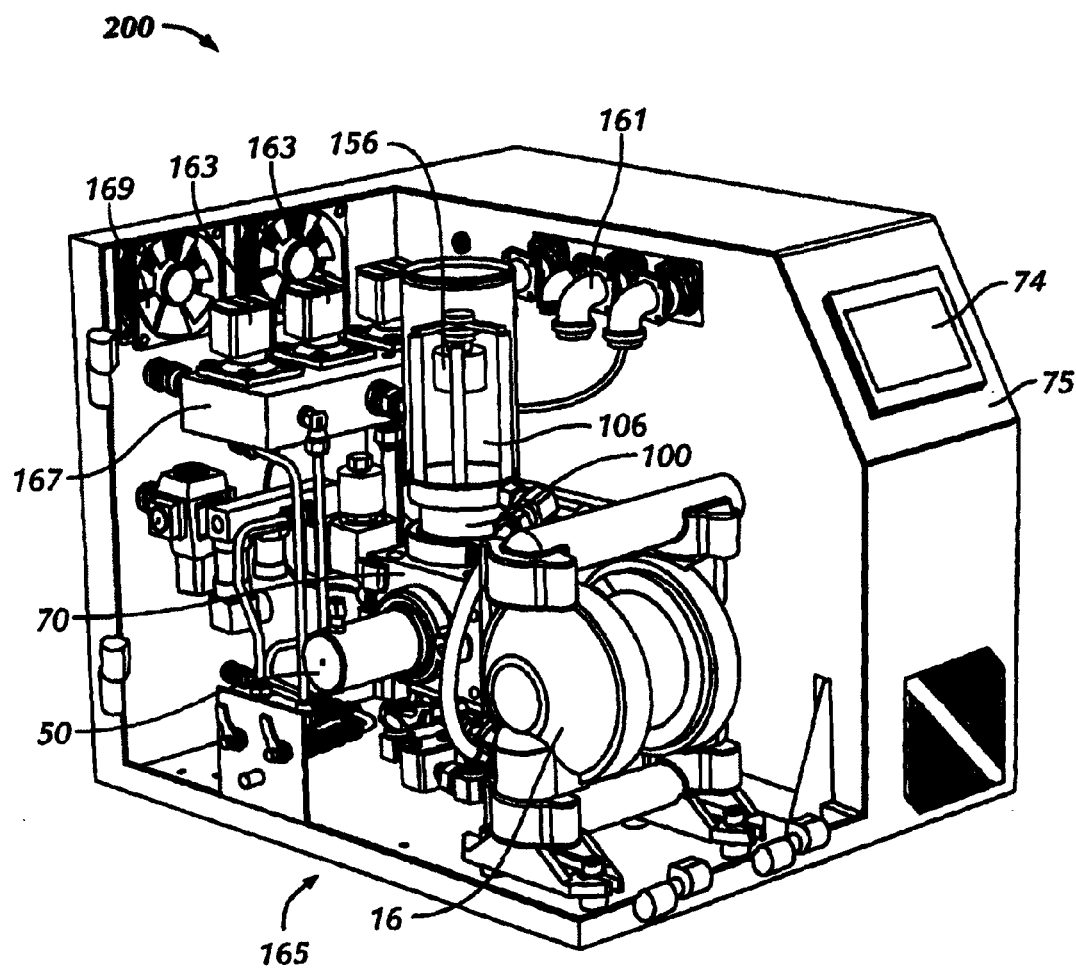
FIGS. 7A-7C are partial perspective views of an automatic drilling fluid property analyzer in accordance with embodiments disclosed herein.
Figure 7B:
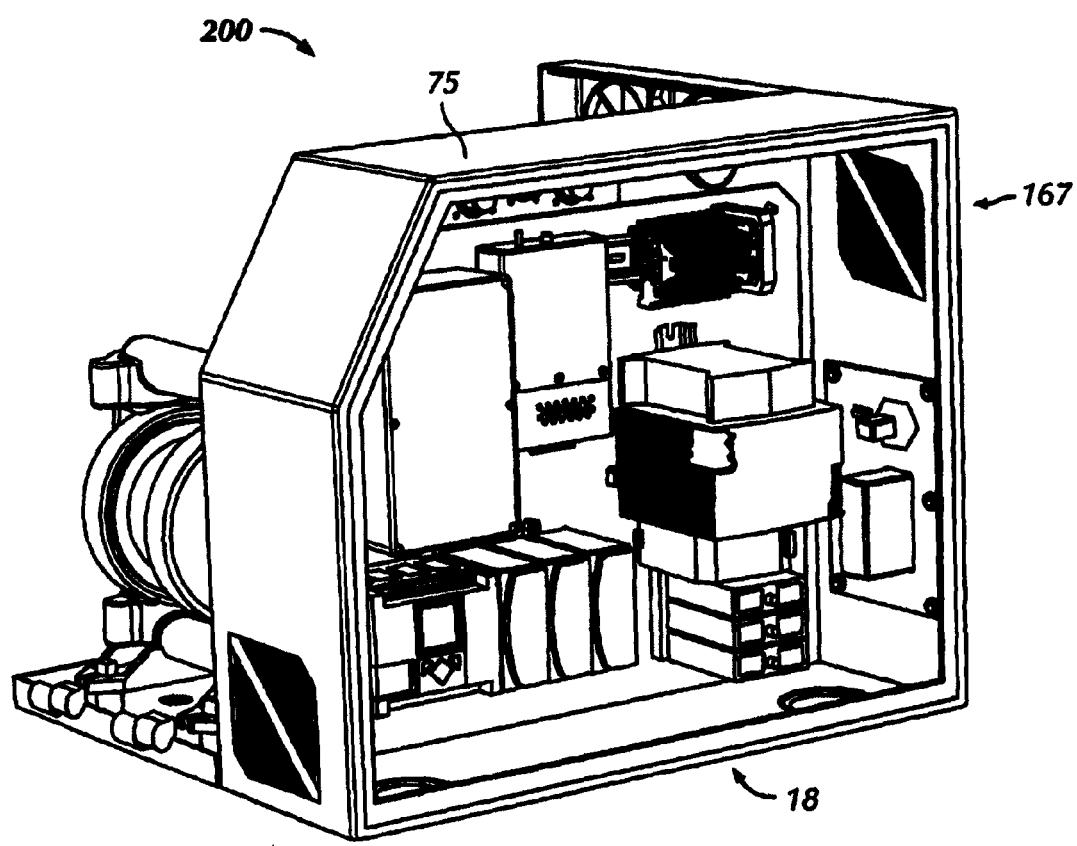

The automatic drilling fluid property analyzer 200 may be disposed in a shell housing 75, as shown in FIGS. 7A and 7B. The shell housing 75 may be divided into two segments, a first area 165 in which the sample housing, automated electrical stability meter 30, and automated viscometer 100 components are housed, and a second area 167 in which an electronic control module 18 is housed. As shown, a housing 156 may be fitted over the motor 106 and torque sensing device 108. Details of the electronics of the electronic control module 18 are discussed in more detail below.

Electrical conduits and wiring 161 may be run between the first area 165 and the second area 167 for electrically connecting various components of the analyzer 200, for example, motor 50, motor 106, torque measuring device 108, valves 163, etc., to the electronic control module 18. Shell housing 75 may include one or more vents and/or fans 169 configured to prevent the analyzer components and electronics from overheating. The valves, 163 may include check valves, as discussed above, which may be disposed in a manifold 167. The manifold 167 may thus include various valves 163, inlets and outlets, thereby controlling the flow of fluid into and out of the analyzer 200.

As shown, the automatic drilling fluid property analyzer 200 also includes a pump 16 for pumping sample fluid into and out of the housing 70 of the analyzer 200 from an active fluid system. One or more solenoid valves 163 are disposed within the shell housing 75 and fluidly connected to the housing 70. The solenoid valves 163 are actuated to allow a sample fluid to fill housing 70 for testing.

Figure 7C:
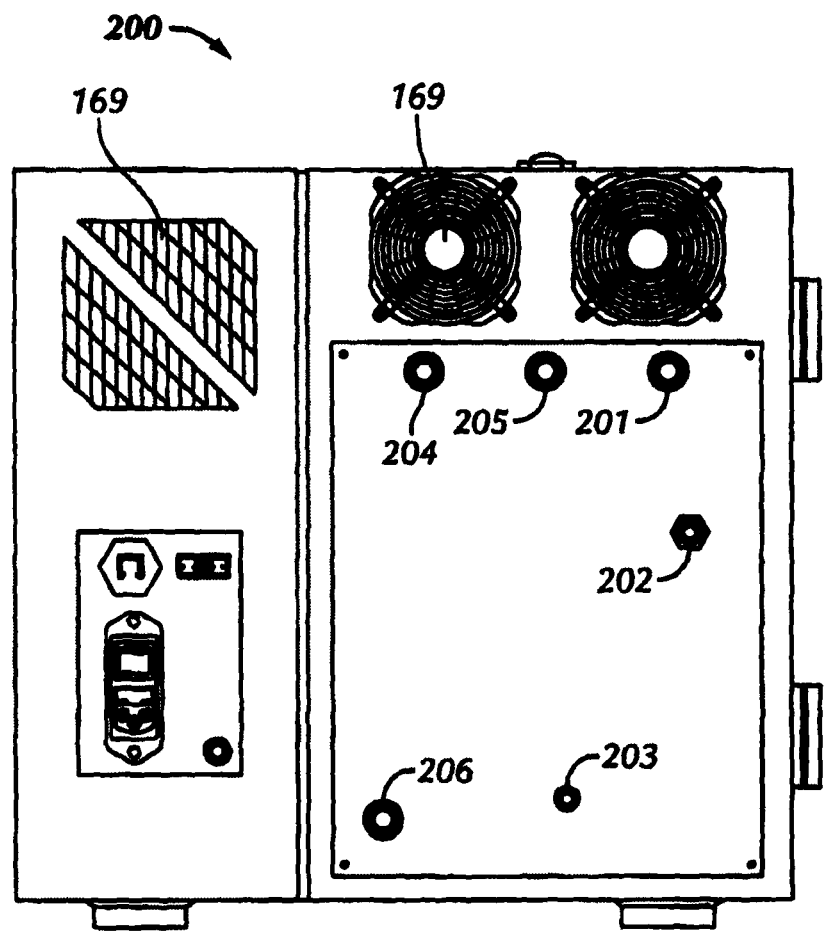

FIG. 7C shows a rear view of the shell housing 75 of the automatic drilling fluid property analyzer 200 having a plurality of plumbing connections for connecting outside fluid lines to various components of the analyzer 200. As shown, the shell housing 75 may include connections for a water line in 201, an air line in 202, a mud line in 204, and a cleaning fluid line in 205. Additionally, connections for waste return 206 and water return 203 may also be provided.

Referring generally to FIGS. 6-7, in some embodiments, automatic drilling fluid property analyzer 200 may also include an alarm system configured to send a signal when an alarm event has occurred. The alarm system may include a plurality of sensors disposed in or proximate various components of the automatic drilling fluid property analyzer 200 and an alarm. For example, a temperature sensor may be disposed in the shell housing 75 and send a signal to the electronic control module 18 when a temperature inside the shell housing exceeds a predetermined maximum value. The electronic control module will then actuate the alarm. The alarm may be a bell, buzzer, electronic sound, or any other alarm known in the art. Additionally, the display 74 of the analyzer may display a message or indicate an alarm event has occurred. The display 74 may specify the type of alarm event. The display may, for example, note that the analyzer has overheated. Examples of alarm events may include a plugged valve, an open door to the shell housing, a low fluid level in the housing, disconnection of a flow line. The alarm system may include various types of sensors, for example, contact sensors, pressure sensors, temperature sensors, position sensors, etc.

In other embodiments of the drilling fluid analyzer, an x-ray spectrometer may be used to determine the content of a sample drilling fluid. For example, a sample may be excited by high energy x-rays or gamma rays, thereby causing the emission of secondary, fluorescent, x-rays. The secondary x-rays may then be analyzed to determine the chemical composition of the sample drilling fluid. The results of the testing may then be transferred to local storage or to a remote facility for processing. Those of ordinary skill in the art will appreciate that other meters may also be used to further analyze drilling fluid samples.

Figure 24:
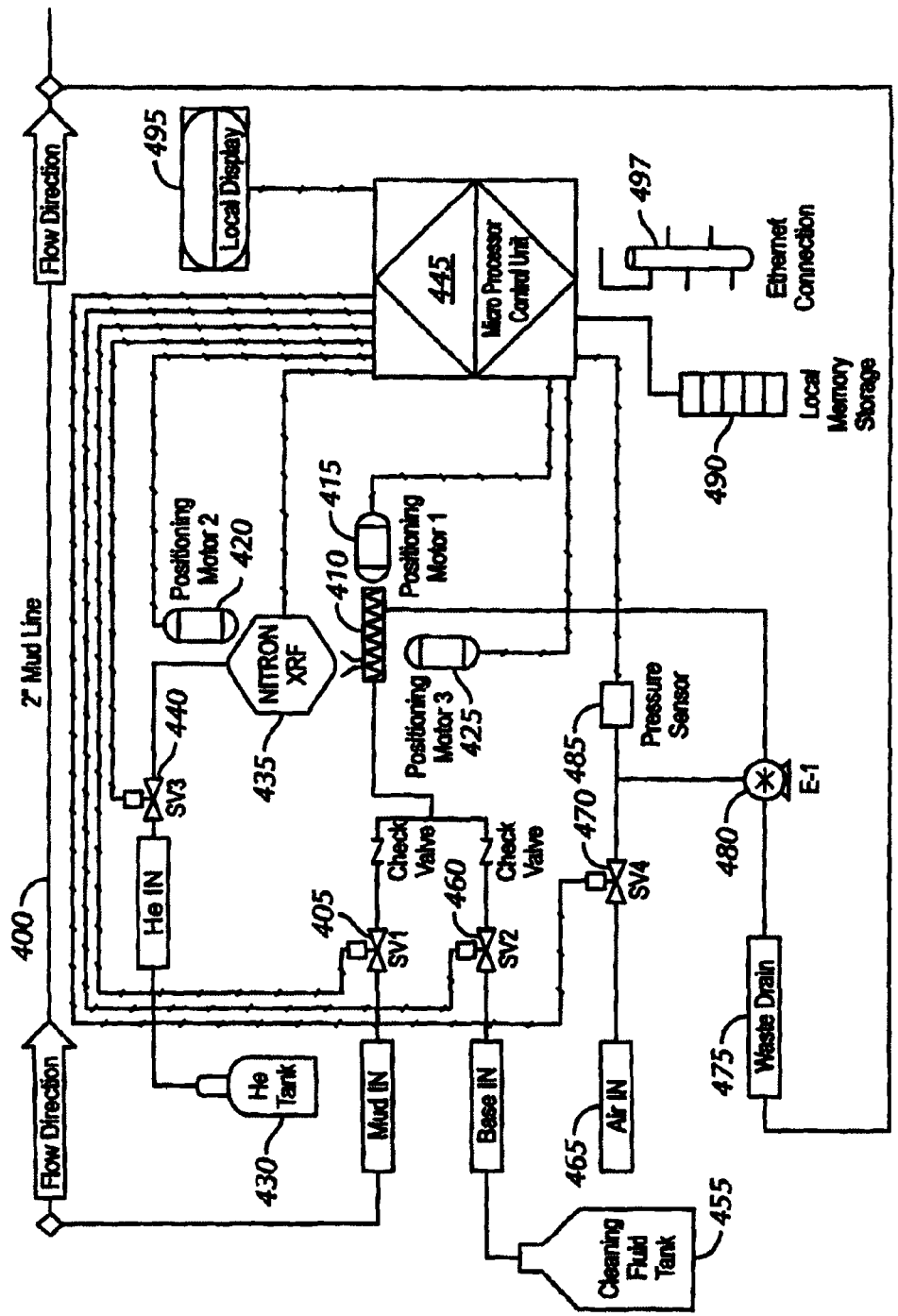
FIG. 24 is a schematic representation of an XRF fluid analyzer according to embodiments of the present disclosure.

Referring to FIG. 24, a schematic representation of a fluid analyzer having an x-ray spectrometer ("XRF") 435 according to embodiments of the present disclosure is shown. In this embodiment, a flow of fluid is directed from an active drilling system flow line 400 through one or more valves 405 and into a test chamber 410. Inside test chamber 410, a slide (450 of FIG. 25) is disposed and configured to move in one or more directions, thereby allowing a sample of drilling fluid to be procured from the active fluid system. One or more motors 415, 420, and 425 may be used to control the orientation of the slide or test chamber 410. As illustrated, motor 415 is configured to move slide laterally in test chamber 410. However, in other embodiments, motor 415 may be used to move slide in more than one direction. The fluid analyzer also includes a helium tank 430 in fluid communication with XRF 435, thereby allowing helium to be used during the analysis. In order to control the flow of helium from helium tank 430 to XRF 435, a solenoid valve 440 may be operatively controlled by a micro processor 445 or PLC.

The fluid analyzer may also include a cleaning fluid tank 455 in fluid communication with test chamber 410. During a cleaning cycle, a fluid, such as a base oil, water, or other fluid containing chemicals such as surfactants may be transferred from the cleaning fluid tank 455 to the test chamber 410. The flow of the cleaning fluid may be controlled by a valve, such as solenoid valve 460. In addition to cleaning fluid, fluid analyzer may include an air system 465 configured to supply air to test chamber 410 or another component of the fluid analyzer. The flow of air may also be controlled with a valve, such as a solenoid valve 470. After a test is complete, the sample fluid may be drained from test chamber 410 through waste drain 475 and back into the active drilling system flow line 400. The sample fluid evacuation may be facilitated though use of a pump 480, air from air system 465, or pushed out of test chamber 410 as new fluid is drawn into test chamber 410. The fluid analyzer may also include various sensors, such as pressure sensor 485, temperature sensors (not shown), or other various sensors for determining the position of the slide within test chamber 410 or a property of the fluid. In certain embodiments, the fluid analyzer may also include various check valves, such as those discussed above, as well are various temperature control apparatuses, such as heating/cooking jackets.

To control fluid analyzer, the system includes micro processor 445 and a local memory storage 490, such as a hard disc drive, flash, or other type of memory known in the art. Data may be displayed and the fluid analyzer may be controlled through local display 495. Additionally, a device for allowing a connection to a network, such as a modem 497, may be used to allow the fluid analyzer to communicate data as well as receive control signals remotely. The remote control aspect of the present disclosure will be explained in detail below.

Figure 25A:
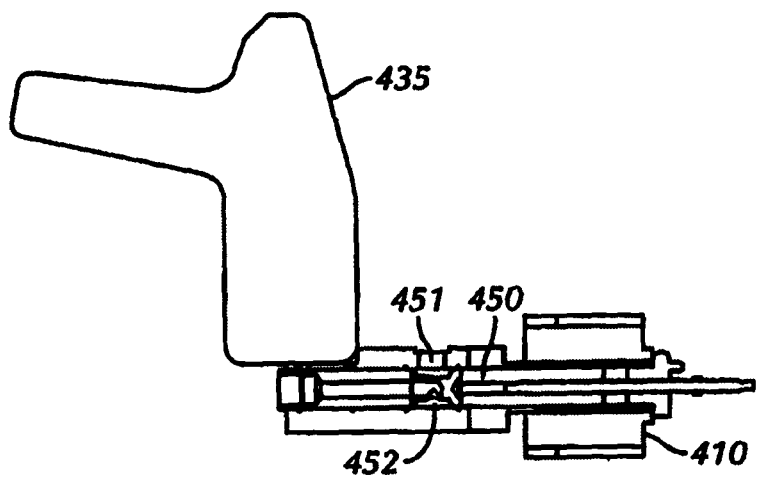
FIGS. 25A-C are cross-sectional views of a test chamber of the XRF analyzer according to embodiments of the present disclosure.
Figure 25B:
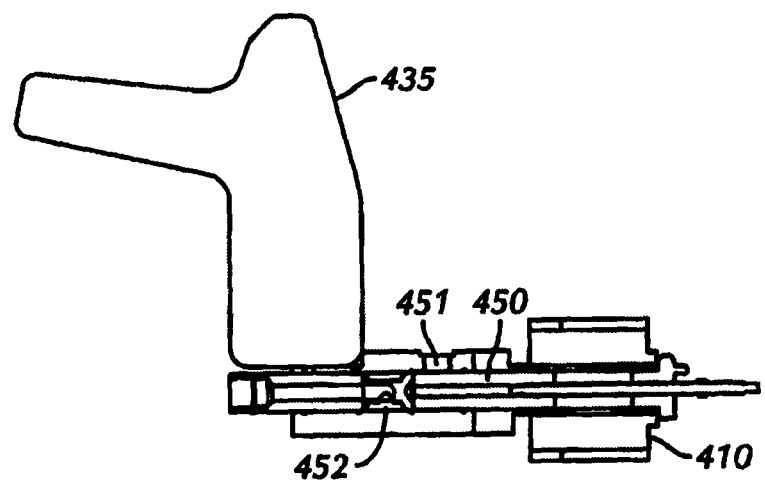
Figure 25C:
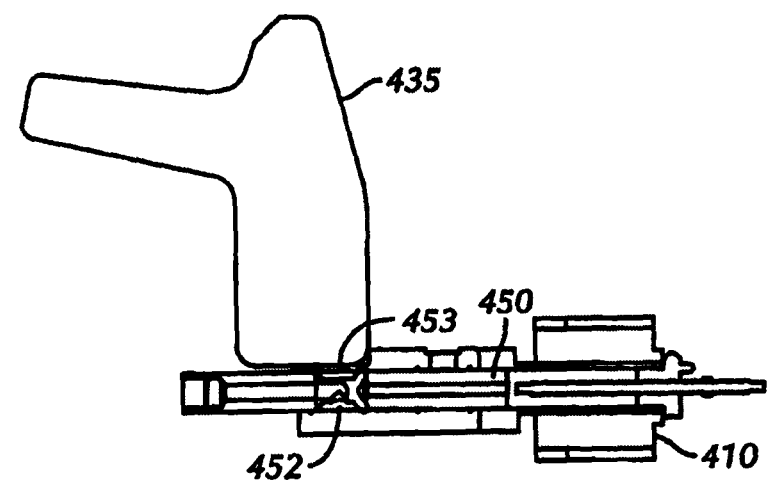

Referring now to FIGS. 25A-C, cross-sectional views of the test chamber and XRF 435 during fill, intermediate, and test positions, respectively, according to embodiments of the present disclosure are shown. In the fill position (FIG. 25A), the slide 450 is in a position to allow fluid to be injected through an injection port 451 into a sample cavity 452. In this embodiment, sample cavity includes approximately a 25 mm opening that allows fluid to flow into the cavity 452. Those of ordinary skill in the art will appreciate that in other embodiments, sample cavity 452 may include openings of different size and/or geometry. One or more of motors (415, 420, or 425 of FIG. 24) may be used to control the orientation of slide 450 within test chamber 410. For example, a motor may move slide 450 laterally in test chamber 410. In the intermediate position (FIG. 25B), slide 450 moves sample cavity 452 including a test fluid out of fluid communication with injection port 451. My moving sample cavity 452 out of fluid communication with injection port 451, fluid is prevented from spilling out of test chamber 410. Thus, the intermediate position may allow the sample size in sample cavity 452 to be controlled. In the test position (FIG. 25C), sample cavity 452 is aligned with test port 453. As sample cavity 452 is not enclosed (enclosing test cavity would prevent accurate XRF analysis), slide 450 should be moved into testing orientation so as to prevent the test fluid from spilling out of sample cavity 452. In the test position, the XRF 435 may be used to analyze the drilling fluid. The sequence of a filling position, an intermediate position, and a test position allows the volume of the sample in sample cavity 452 to be maintained. The sequence also prevents fluid from overflowing from sample cavity 452 as the intermediate position is closed from the rest of the system, thereby preventing the injection side and the testing side of the system to be open at the same time.

Because XRF testing is sensitive to the location of the sample being tested, the motors (415, 420, and 425 of FIG. 24) may be used to ensure that the orientation of sample cavity 452 to XRF 435 is within a specific tolerance. By using an XYZ orientation analysis, the fluid analyzer can ensure that fluid sample tests are not distorted by blockage of the sample, as well as ensure that the sample does not overflow sample cavity 452. Referring briefly back to FIG. 24, in an embodiment wherein motor 415 controls slide 450, slide 450 may be moved laterally within test chamber 410 to move a sample fluid from fluid communication with injection port 451 into orientation with test port 453. During testing, motors 420 and 425 may be configured to change the orientation of either test chamber 410 or XRF 435, thereby allow multiple tests from a single sample to be procured. Because the focal length between the XRF and the sample is important to maintain consistent and comparable results, the motors 415, 420, and 425 may work in concert to ensure that the distance between the sample fluid and test port 453 remains relatively constant. In certain embodiments, the gap between the XRF and the sample may be between 0.5 mm and 1.0 mm. Depending on the specifications of the XRF, this gap may be increased or decreased, thereby allowing the system to be customized to analyze particular fluids. In certain embodiments, the motors may be used to adjust the position of the XRF, thereby allowing multiple samples to be procured. In such an embodiment, the XRF may move in a substantially circular path, thereby allowing various portions of the sample to be tested. Specifically, the XRF may move laterally across the surface of the sample, while maintaining the same height above the sample, thereby allowing various readings to be taken across the surface of the sample. Additionally, because multiple readings of each sample may be procured, false readings may be avoided. For example, in certain embodiments, multiples readings are procured and a statistical average is performed or account for anomalies in the various readings.

Additionally, the temperature of the test chamber 410 and the sample may be controlled, thereby maintaining a constant volume of fluid and allowing the distance between the sample and XRF 435 to be the same among various tests. The temperature may be controlled by disposing a fluid conduit (not shown) in test chamber 410 proximate sample cavity 452. A fluid, such as water, having a known and controlled temperature may be run through the fluid conduit thereby allowing the temperature of the sample fluid to be controlled. Controlling the sample fluid may help ensure that the XRF test is accurate between multiple samples. By controlling the location of the sample relative to XRF 435 and controlling the temperature, the results of the tests may be more accurate and provide better comparability between the results of multiple tests.

Figure 26A:
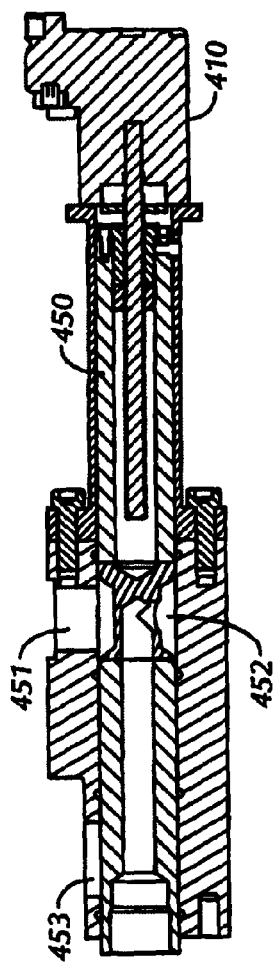
FIGS. 26A-C are cross-sectional views of a test chamber of the XRF analyzer according to embodiments of the present disclosure.
Figure 26B:
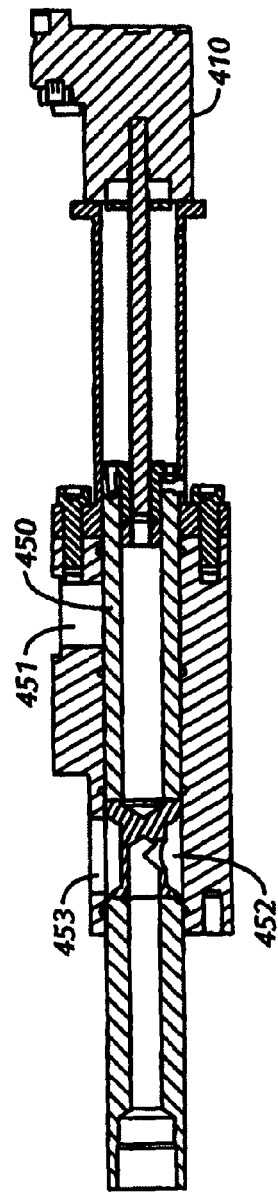
Figure 26C:
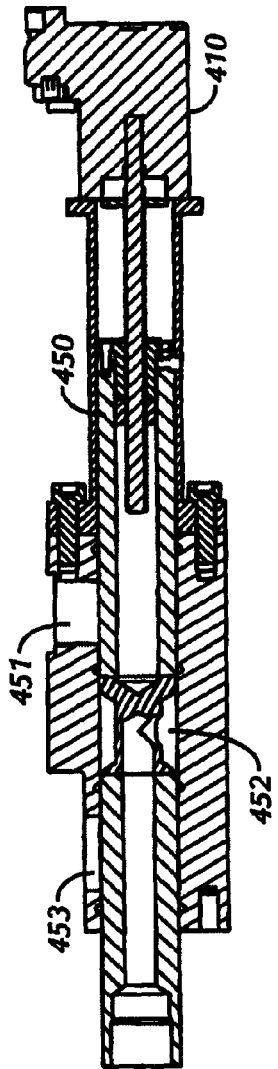

Referring to FIGS. 26A-C, a cross-sectional view of the test chamber in fill and test positions, respectively, according to embodiments of the present disclosure are shown. During a testing process, slide 450 begins in a fill position (FIG. 26A), and a fluid solenoid (not shown) and an air solenoid (not shown) are opened, thereby allowing a sample of fluid to be injected from the active drilling fluid system into sample cavity 452. When sample cavity 452 has the desired volume of fluid, the air and fluid solenoids are closed, thereby stopping the flow of fluid into test chamber 410. Slide 450 is then moved into test position (FIG. 26B), such that sample cavity 452 is aligned with test port 453 and is configured to allow the XRF (not shown) to run a test sequence. After the test sequence, a pump (not shown) is actuated along with opening of the air solenoid, thereby purging sample cavity 452 of the sample fluid. When sample cavity 452 is purged, the pump is stopped and slide 450 is moved back into the fill position. Between the fill position and the test position, the sample may be held in an intermediate position (FIG. 26C). In the intermediate position, the sample may be temporarily held to allow the fluid to stabilize, thereby preventing an overflow. Depending on the properties of the fluid, the hold time may vary, for example, in certain embodiments, the sample is in an intermediate position between 5 seconds and 10 minutes, and in specific embodiments, the sample is in the test position for approximately 30 seconds.

Once in the fill position (FIG. 26A), a base oil cleaner may be injected into test chamber 410 and into sample cavity 452 by opening a base solenoid (not shown). The pump is then re-actuated, thereby purging any residual fluid or particulate matter from test chamber 410. Slide 450 may then be moved back into the test position (FIG. 26B), and the pump actuated via opening of the air solenoid to further remove residual fluid and/or particulate matter from test chamber 410. At this point, a subsequent fluid test may be performed. Those of ordinary skill in the art will appreciate that depending on the type of fluid being tested, the sequence of fill and test positions may vary. For example, in certain operations, only a single purge cycle may be required, while in other operations, three or more purge cycles may be required to adequately purge residual fluid and particulate matter from test chamber 410.

Additional components may be included, such as a valve (not shown) on sample cavity 452, which may be closed when the fluid is being tested. When such a valve is in a closed position, fluid would not be allowed to evacuate sample cavity 452, thereby ensuring the sample volume remains constant. Opening of the valve may allow the fluid to be removed from sample cavity 452, such as during a cleaning cycle. Other components may include cleaning devices. An example of a cleaning device that may be used with embodiments of the present disclosure is a wiper (not shown) disposed on or proximate test chamber 410. The wiper may be used to clean injection port 451, sample cavity 452, or other portions of the system. In certain embodiments, the wiper may be disposed on slide 450, thereby allowing both internal and external components of test chamber 410 to be cleaned. Additionally, a pump (not shown), such as a pneumatic pump may be in fluid communication with sample cavity 452. The pump may be used to draw fluid into or out of sample cavity 452 during filling and cleaning cycles.

During XRF testing, a single sample may be tested multiple times. For example, once in the test position, the XRF 435 may be moved relative to test chamber 410 by actuation of one or more motors, thereby allowing the focus of the XRF to shift relative to sample cavity 452. Because the portion of the sample fluid being tested is small relative to the total surface area of the sample exposed through sample cavity 452, multiple tests not including an overlapping sample portion may be performed. In other embodiments, XRF 435 may be held in a constant position and test chamber 410 may be moved relative to XRF 435, thereby providing another way for multiple tests to be performed. In still another embodiment one or more motors may be used move slide 450 relative to test chamber 410 and/or XRF 435. In such an embodiment, the test chamber 410 and XRF may be held stable, and only slide 410 would be movable.

The XRF analyzer may be combined with the various other testing apparatuses described above, thereby allowing a single fluid analyzer to have a viscometer, electrical stability monitor, and XRF monitor. In such a configuration, the XRF may be disposed either before or after the viscometer or electrical stability monitor, as well as in a configuration to allow the separate tests to occur simultaneously.

As explained above, in order to conduct a stability test, fluid is drawn into a closed chamber having an electrical stability probe and a wiper that can be rotated into the gap in the probe to clean residue therefrom. In order to draw the fluid into the chamber, a series of solenoid valves work in conjunction with a pump, thereby allowing the volume of fluid in the chamber to be controlled. Once an acceptable temperature is reached, a test sequence is initiated. After the test is complete, the test fluid is withdrawn from the chamber and replaced with a cleaning fluid. To clean the device, a wiper is actuated with cleaning fluid present to remove residue that may have settled on the probe. In order to control the testing and cleaning, a programmable logic controller ("PLC") or micro processor is operatively coupled to the device, as will be explained in detail below.

Figure 27:
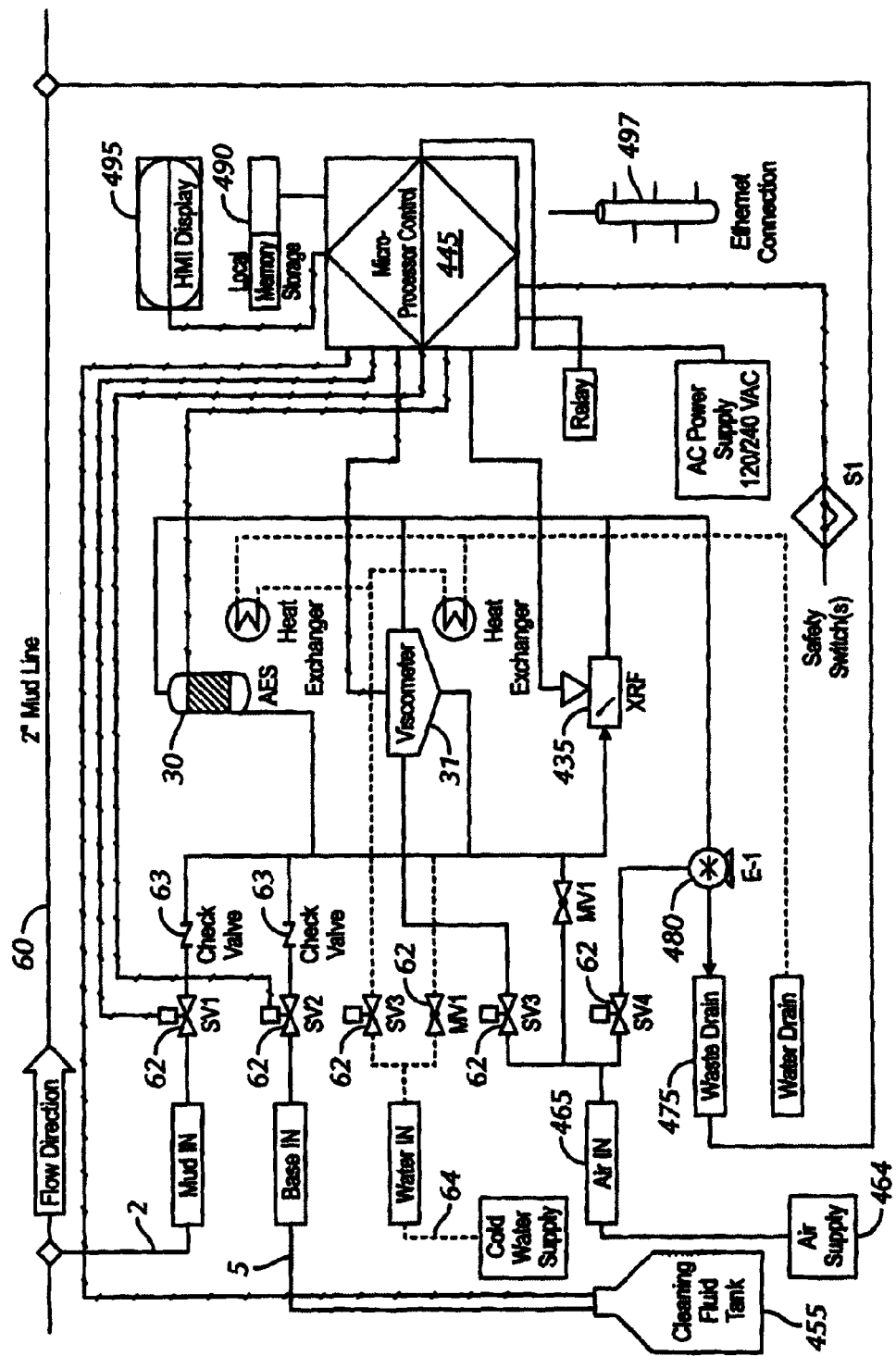
FIG. 27 is a process and instrumentation diagram of a combination analyzer in accordance with embodiments disclosed herein

To further explain the operation of a combined electrical stability, viscometer, and XRF analyzer, FIG. 27, which is a process and instrumentation diagram for such a system is discussed below. As illustrated, an automated electrical stability meter 30, a viscometer 31, and an XRF analyzer 435 are placed in line with an active fluid system 400. A plurality of valves 62 control the flow of fluids in and out of the automated electrical stability meter 30, a viscometer 31, and an XRF analyzer 435. In certain embodiments, valves 62 may be solenoid valves, while in other embodiments, valves 62 may include check valves 63, as discussed in detail above. Depending on the operational requirements of the system, a combination of solenoid 62 and check valves 63 may be used in certain systems. For example, as illustrated, fluid inlet line 2 and base fluid inlet line 5 are configured to provide a flow of fluid through solenoid valves 62 and then through check valves 63. Thus, fluids that may include particulate matter that may clog valves 62 may flow through check valves 63. However, water inlet 64 flows though valves 62 not including check valves 63. Those of ordinary skill in the art will appreciate that in alternate embodiments, water inlet 64 may also flow through check valves 63.

During operation fluid may flow through fluid inlet line 2 and into one or more of the automated electrical stability meter 30, a viscometer 31, and an XRF analyzer 435. Those of ordinary skill in the art will appreciate that depending on the type of test required, fluid may flow into one, two, or all three of the analyzers, thereby allowing multiple tests to be performed simultaneously. In certain embodiments, it may be desirable for fluid to be tested by all three analyzers, while in other embodiments, only one or two of the tests may be run. Additionally, while FIG. 27 illustrates the analyzers being disposed in serial fashion, in alternate embodiments, multiple inlet lines may be used such that fluid may flow substantially simultaneously into each of the meters, or at least two of the meters.

As explained above, the system also includes a cleaning fluid tank 455 that is configured to provide a flow of base fluid to the automated electrical stability meter 30, a viscometer 31, and an XRF analyzer 435, thereby allowing the analyzers to be cleaned between tests. The system also includes a pump 480 that is configured to remove tested fluids and cleaning fluids from the automated electrical stability meter 30, a viscometer 31, and an XRF analyzer 435. The pump 480 may be used to pump fluids to waste drain and, in certain embodiments, back into active fluid system 400. The system may further include an air supply 464 connected to an air inlet 465, thereby allowing air to be injected into one or more of the automated electrical stability meter 30, a viscometer 31, and an XRF analyzer 435.

The automated electrical stability meter 30, a viscometer 31, and an XRF analyzer 435 are also operatively connected to a micro-processor control 445, thereby allowing the analyzers to collect and process data. The micro-processor control 445 is operative connected to a local storage memory 490 and a display 495, thereby allowing collected and processed data to be stored and/or displayed. In certain embodiments, micro-processor control 445 may also be operatively connected to a remote connection 497, such as an Ethernet connection, thereby allow collected and/or processed data to be sent or received remotely.

Those of ordinary skill will appreciate that, in view of the present disclosure, various combinations of analyzers may exist. For example, in certain embodiments, a system having all three of the automated electrical stability meter 30, a viscometer 31, and an XRF analyzer 435 may be used. In alternate embodiments, a system may include only the automated electrical stability meter 30 and the viscometer 31, the automated electrical stability meter 30 and the XRF analyzer 435, or the viscometer 31 and the XRF analyzer 435.

Generally, the present disclosure is directed to a computer-assisted method for automated drilling fluid property analysis. The drilling fluid properties that may be analyzed/determined include viscosity, gel strength, and electric stability. Multiple configurations of drilling fluid analyzers are within the scope of the present disclosure. For example, in certain embodiments, the drilling fluid analyzer may be configured to determine electric stability, while in other embodiments the drilling fluid analyzer may be configured to determine gel strength, viscosity, or combinations thereof. Regardless of whether the drilling fluid analyzer is configured to determine one or more combinations of electric stability, gel strength, and/or viscosity, the system for determining the properties will be operatively connected to a computer for the determination of the specific property or properties. The computer, whether local or remote, includes a software application executing on a processor.

The software application includes instructions for causing a drilling fluid to be transferred from an active fluid system to a sample cell. The amount of drilling fluid transferred may vary depending on the requirements of a particular operation; however, generally, a 0.5 liter sample will be transferred from the active drilling fluid system to a sample cell of the fluid analyzer. After the sample cell is filled with a desired amount of fluid, the fluid may be directed into contact with electrodes of an electric probe. As a voltage is applied across the electrodes of the electric probe, the fluid analyzer determines when the fluid conducts a charge across the electrodes, the data is recorded, and an electric stability may be determined based on the applied voltage. Those of ordinary skill in the art will appreciate that the above method will allow for the determination of the electric stability, and thus the emulsion stability of oil-based or synthetic-based drilling fluids.

In certain embodiments, the recorded data may be stored locally until testing is complete, while in other embodiments, the data may be transferred to a remote data store for either storage or remote processing. Depending on the amount of data, number of tests, etc., the data maybe be transferred after each test or in batches.

The length of the test may vary based on the properties of the drilling fluid. For example, a single test may last 30 minutes or longer in certain embodiments, while in other embodiments, a new test may be performed every couple of minutes. In order to increase the accuracy of the determined drilling fluid property, a single sample fluid may be tested multiple times. For example, a single fluid may be tested five times, and if any outlier results are detected, the outlier results may be excluded from the sample results used in determining the final fluid property.

After the test is performed, the fluid analyzer may perform a cleaning cycle, by discharging the fluid sample and injecting a cleaning fluid into the sample cell. The cleaning fluid may include a base oil, such as diesel, mineral oil, or other bases to the particular fluid in the active drilling fluid system, or may include other additives, such as surfactants or water to further clean the sample cell. During the cleaning cycle, the wiper may be rotated through the probe, thereby cleaning the surfaces of the probe, as well as agitating the cleaning fluid in the sample cell to remove particulate matter that may have settled on other surfaces of the sample cell.

The time the cleaning fluid remains in the sample cell may be modulated based on particular properties of the fluid. For example, a fluid with high viscosity may require a longer cleaning cycle, or fluids with high levels of low gravity solids or weighting agents that may adhere to the surfaces of the sample cell may require longer cleaning cycles to thoroughly remove. The cleaning cycle may includes multiple rotations of the wiper, as well as one or more additions of cleaning fluid to the sample cell. In certain embodiments, the cleaning cycle may also include additions of water or air to further remove a tested fluid sample from the sample cell prior to sampling of a subsequent fluid sample.

After the sample cell is clean, the fluid analyzer may be instructed to discharge the cleaning fluid and transferred a second sample from the active drilling fluid system into the sample cell. Depending on the specifics of the operation, a specified volume of drilling fluid may be cycled from the active drilling system through the fluid analyzer prior to filling the sample cell, thereby ensuring that the second sample does not contain residual fluid remaining in the line from the original test. For example, in certain embodiments, fluid may be allowed to run through the fluid analyzer from the active drilling system for a set period of time or until a specific volume of fluid has passed through the system. When it is determined that the fluid passing through the system is acceptable for sampling, the sample cell is filled, and a second test cycle may begin.

In other embodiments, the fluid analyzer may also include a viscometer configured to allow the fluid analyzer to collect data for determining the gel strength and/or viscosity of a sample drilling fluid. Similar to the test described above, after a sample fluid is transferred from the active drilling fluid system into the sample cell, the fluid is directed to an area between a sleeve and bob of a viscometer. Depending on the configuration of the viscometer, either the sleeve or bob is rotated at a specific speed. The response of the fluid to the rotational speed of the sleeve or bob is recorded, and the data is either stored or sent to a remote computer system for processing, as described above with respect to the electric stability test.

The rotational speed of the sleeve or bob may also be varied in order to more accurately determine the gel strength of the fluid. For example, the sleeve or bob may be rotated at 3, 6, 300, and/or 600 revolutions per minute ("RPM"). Those of ordinary skill in the art will appreciate that the rotational speed may vary based on the specifics of the drilling operation or the requirements of the analysis.

In certain embodiments, both electric stability tests and viscosity and/or gel strength tests may occur substantially simultaneously. Thus, the length of time required for the test may be decreased. Additionally, other steps may occur before, after, or during a specific test. For example, a temperature of the sample fluid may be adjusted, and/or the sample cell may be pressurized. The test may also be adjusted via a remote computer during the test if an operator determines that the fluid analyzer is not performing as desired.

The progression of the test, including the specific parameters of the test, may be pre-programmed, such that the tests may be fully automated. For example, a drilling operator may adjust specific fluid analyzer parameters including the number of tests to be performed on a single sample, the number of samples to be tested, the frequency of the tests, the sample size to be tested, the temperature of sample fluid, the voltage applied, the rotational speed of the viscometer, the pressure applied to the sample cell, number of cleaning cycles, type of cleaning cycle, etc. The specific parameters may then be input as a test package, either locally or remotely, and the fluid analyzer may automatically being testing. Should a condition occur that requires manual adjustment, a local operator or remote operator may override the programming, adjusting one or more of the analyzer parameters, thereby allowing for optimization of the testing.

As explained above, the fluid testing may include a series of tests that are preprogrammed either from a remote location or from a local control. In order to control and/or monitor the testing, a drilling operator may also have one or more control panels showing multiple displays. The graphical user interface ("GUI") that is displayed to an operator may change based on the particulars of the operation; however, exemplary GUIs are described below as an indication as to the type of displays that may be used.

Figure 8:
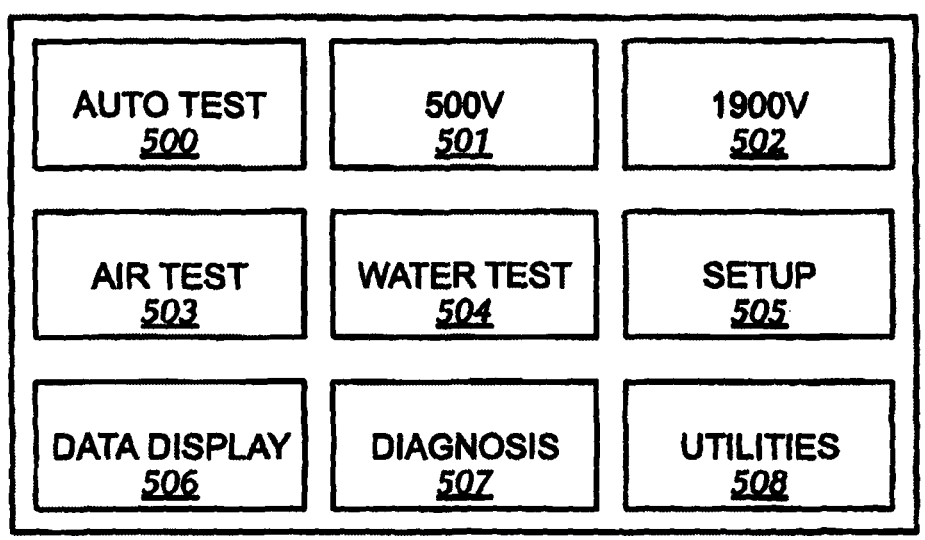

Referring initially to FIG. 8, a local display according to embodiments of the present disclosure is shown. In this embodiment, the local display includes a menu for selecting specific types of tests, calibration modes, etc. As illustrated, local display may include an auto test selector 500, a 500V selector 501, a 1900V selector 502, an air test selector 503, a water test selector 504, a setup selector 505, a data display selector 506, a diagnostic selector 507, and a utilities selector 508.

Figure 9:
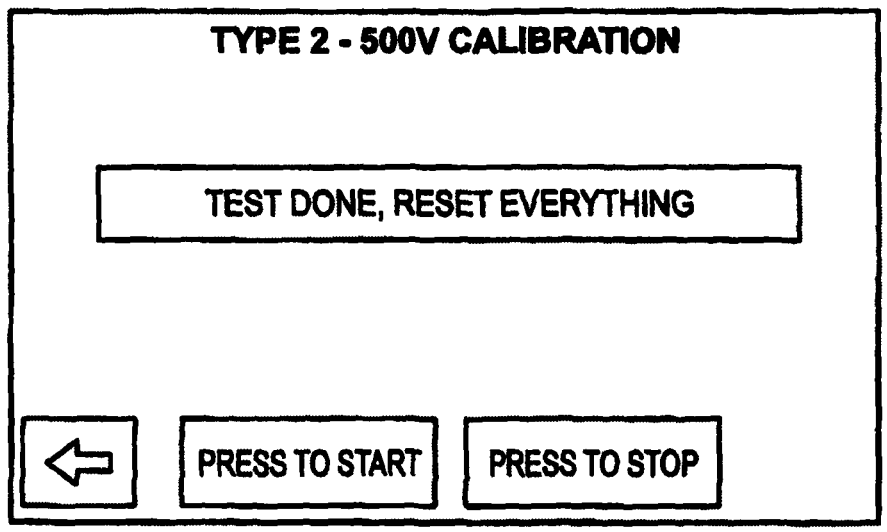
Figure 10:
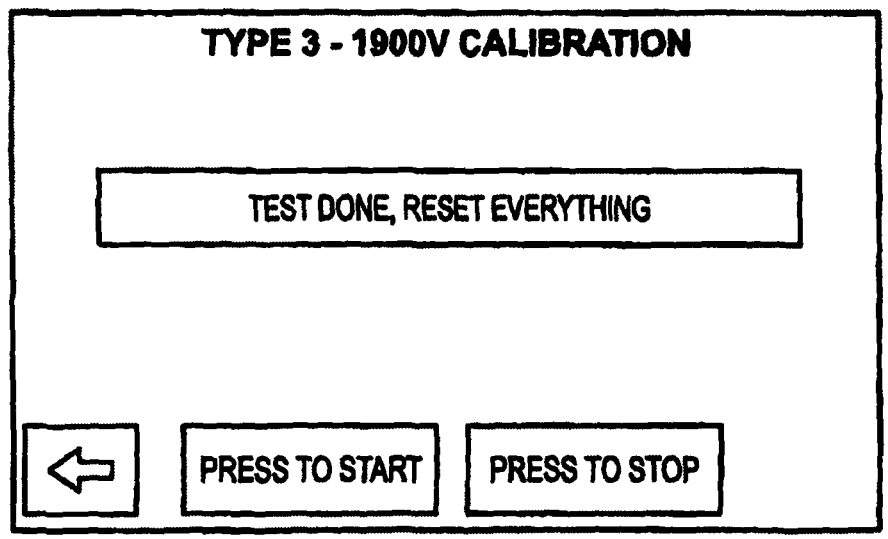

Prior to operation, one or more test cycles may be programmed, thereby allowing for automation of the entire testing process. In addition to test cycles, calibration tests may also be performed. For example, in one embodiment, the device includes a 500V test that allows the operator to verify the calibration of the probe against an internal resistor network. The device may also include a 1900V test that allows the operator to verify the calibration of the probe against an internal resister network. The results of the tests may be displayed on a data display page such as that displayed in FIGS. 9 and 10.

Other embodiments may include an air test and/or a water test. As air is a relatively good insulator, the test should result in a high voltage reading of approximately 1900V and fall within about 2.5% of the 1900V requirement. As water is a conductor, the test should result in a high voltage reading of approximately 500V and fall within about 2.5% of the 500V requirement. If the tests do not fall within an acceptable range, the operator may be notified that the device is not in condition to perform automated testing.

During calibration of the device, a cleaning cycle is initially performed. In the cleaning cycle, existing fluid in the chamber is discharged, cleaning fluid fills the chamber, and the probe is automatically cleaned. After the cleaning cycle, an electronics test is performed, in which the probe is internally disconnected and the voltage is ramped up to a maximum. After the electronics test, an air test is performed, in which cleaning fluid is discharged from the chamber, air is allowed to fill the vessel, and the probe is reconnected and voltage is ramped up to maximum. After the air test is performed, a water test is performed, in which the test vessel is filled with water, the voltage is ramped up, and the electrical stability threshold of 3V is compared to the test voltage. The last step in calibration is determining meter accuracy. In this step, the probe is disconnected and internal resisters and Zener diodes are used to check the accuracy of the meter running at 500 VAC and 1900 VAC.

In order to setup a test, a number of different options may be selected by the operator. Referring to FIGS. 11 and 12, example setup test displays according to embodiments of the present disclosure are shown. Initially, an operator may determine a number of profiles correspond to the number of tests that will be performed. The user may also select a number of ramps, number of wipes, mud transfer in duration, cool down duration, temperature hold times, delay between ramps, cycle delays, pressure set points, base fluid in duration, base soak durations, and various temperature set points. Each selection may be adjusted based on the requirements of the drilling operation and/or the requirements of a particular test.

Figure 13:
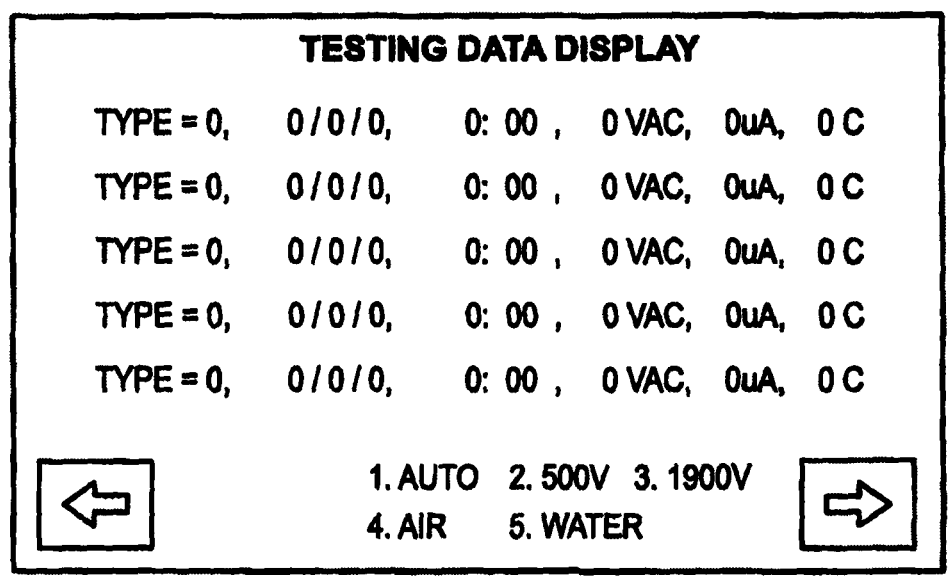

Referring to FIG. 13, the local display may be selected so a viewing may observe current testing data. Other displays that an operator may select to view include a system status page, such as that displayed in FIGS. 14 and 15. The systems status page may allow an operator to view the condition of the wiper, motor, structure of the unit, condition of one or more valves, the condition of the relays, a voltage reading, current reading, temperature reading, and/or pressure reading.

Navigating between the different displays may be achieved via multiple types of interfaces such as, for example, peripheral devices, keyboard, and/or touch screens. Those of ordinary skill in the art will appreciate that all of the discussed displays as well as additional displays may be present in a particular device, depending on the requirements of a drilling operation.

As explained above, the device may have a local display, as well as a remote display. The remote display allows the device to be controlled and the testing monitored remotely. Different methods of establishing a connection between the device and a remote control facility may be used. In one embodiment, the device may be connected to an Ethernet network, thereby allowing device to be accessed remotely over the Internet. In other embodiments, the device may be connected through a virtual private network ("VPN"), thereby allowing connection between the device and any personal computer logged into the network. In still another embodiment, the device may be accessed remotely by connecting the device to a network router.

Figure 16:
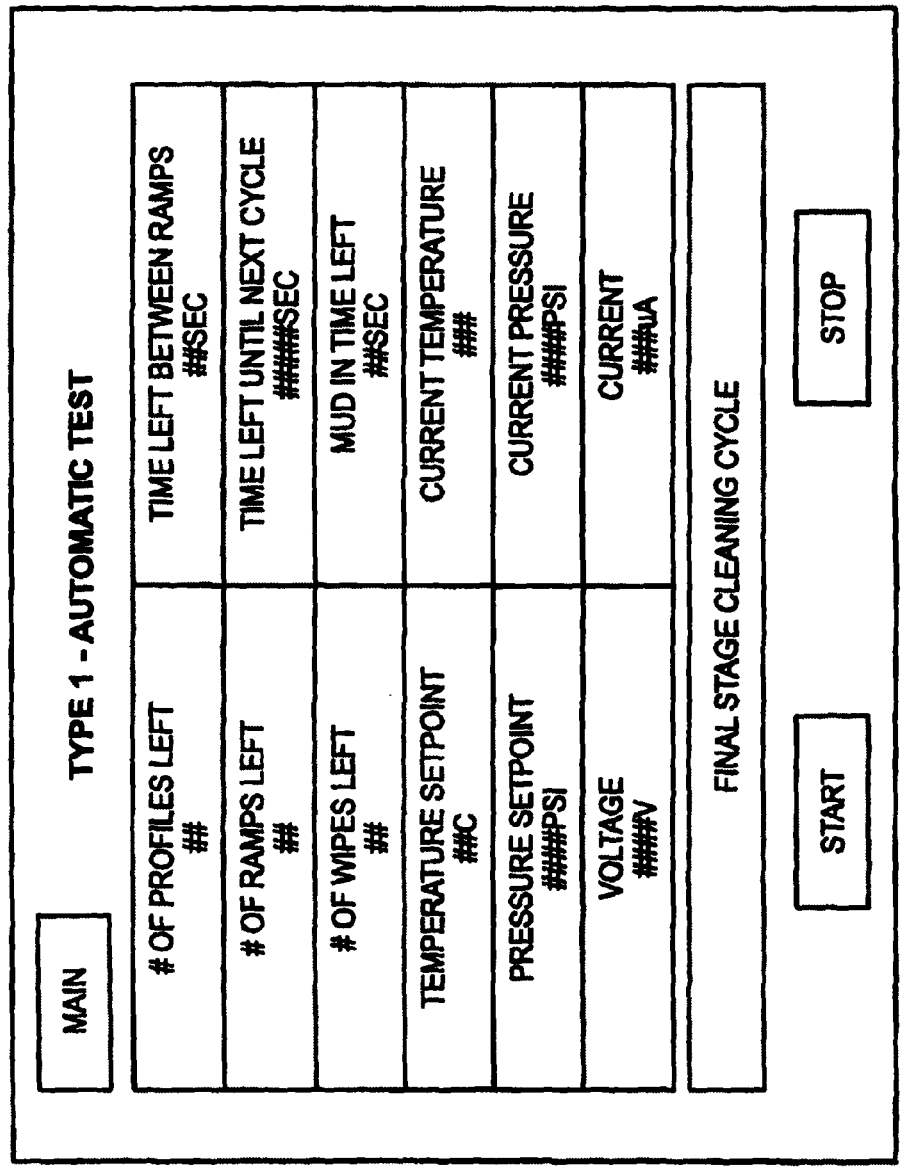
Figure 17:
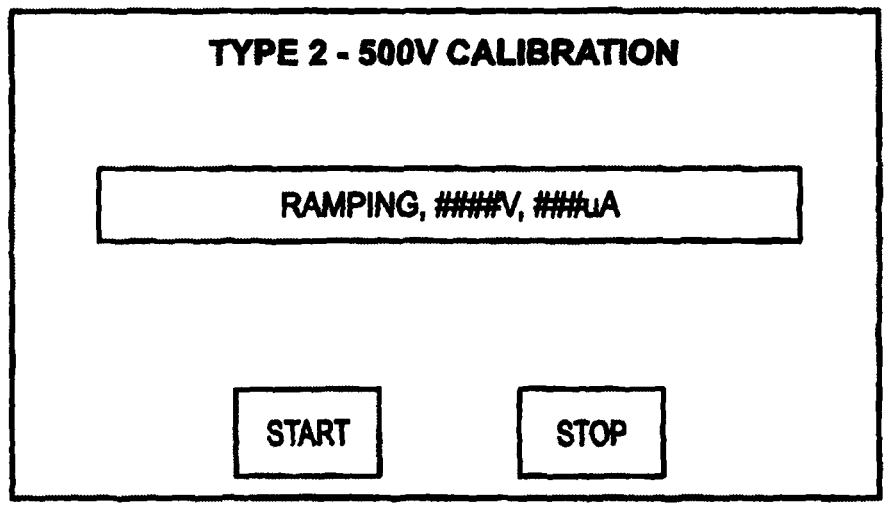
Figure 18:
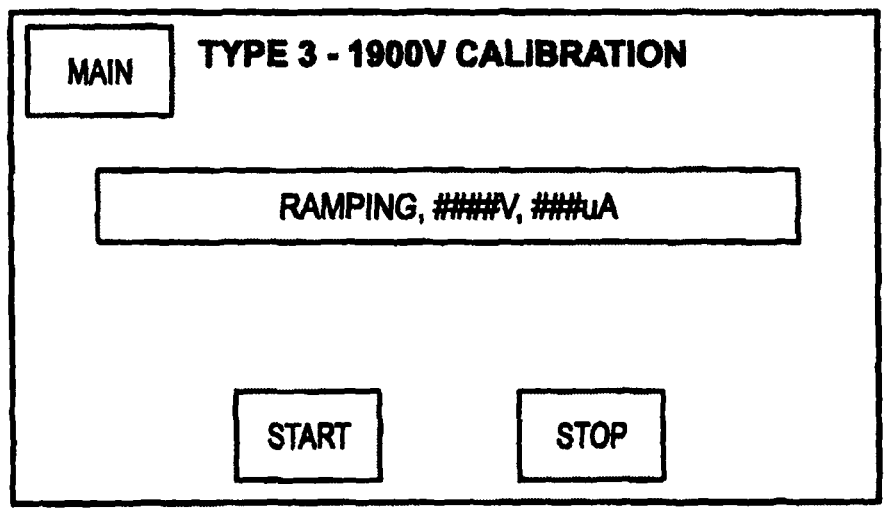
Figure 21:
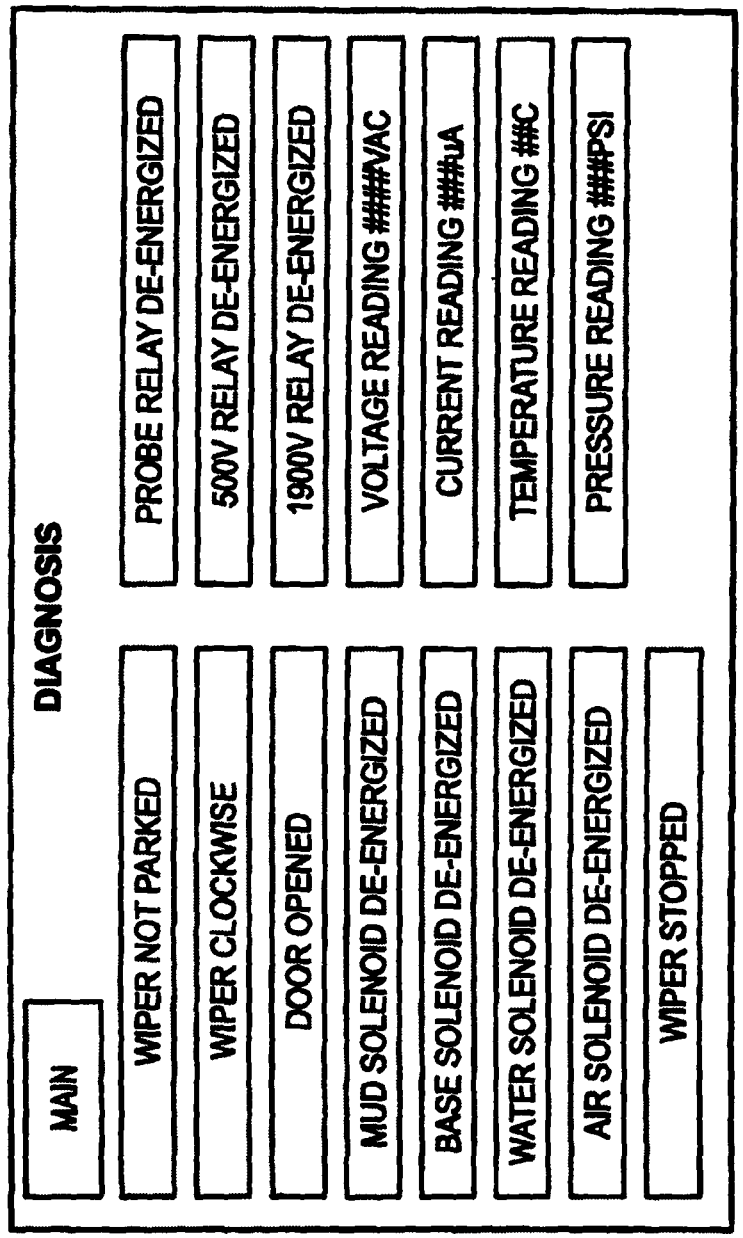

While operating in remote mode, an operator may monitor and/or control the testing, including, for example, initiating calibration tests, inputting testing parameters, loading new testing profiles, and viewing the results of the test. Examples of remote displays are illustrated in FIGS. 16-21. FIG. 16 is a display of an automatic results page, FIGS. 17 and 18 are displays of calibration modes, FIG. 19 is a display of the setup screen, FIG. 20 is a display of the test data screen, and FIG. 21 is a display of a diagnostics screen.

Those of ordinary skill in the art will appreciate that the specific displays may vary according to the specific components of the device. While the displays discussed above are specific for a device for testing electrical stability of a fluid the same and additional options may be available for a device capable of determining gel strength and/or viscosity.

Figure 22:
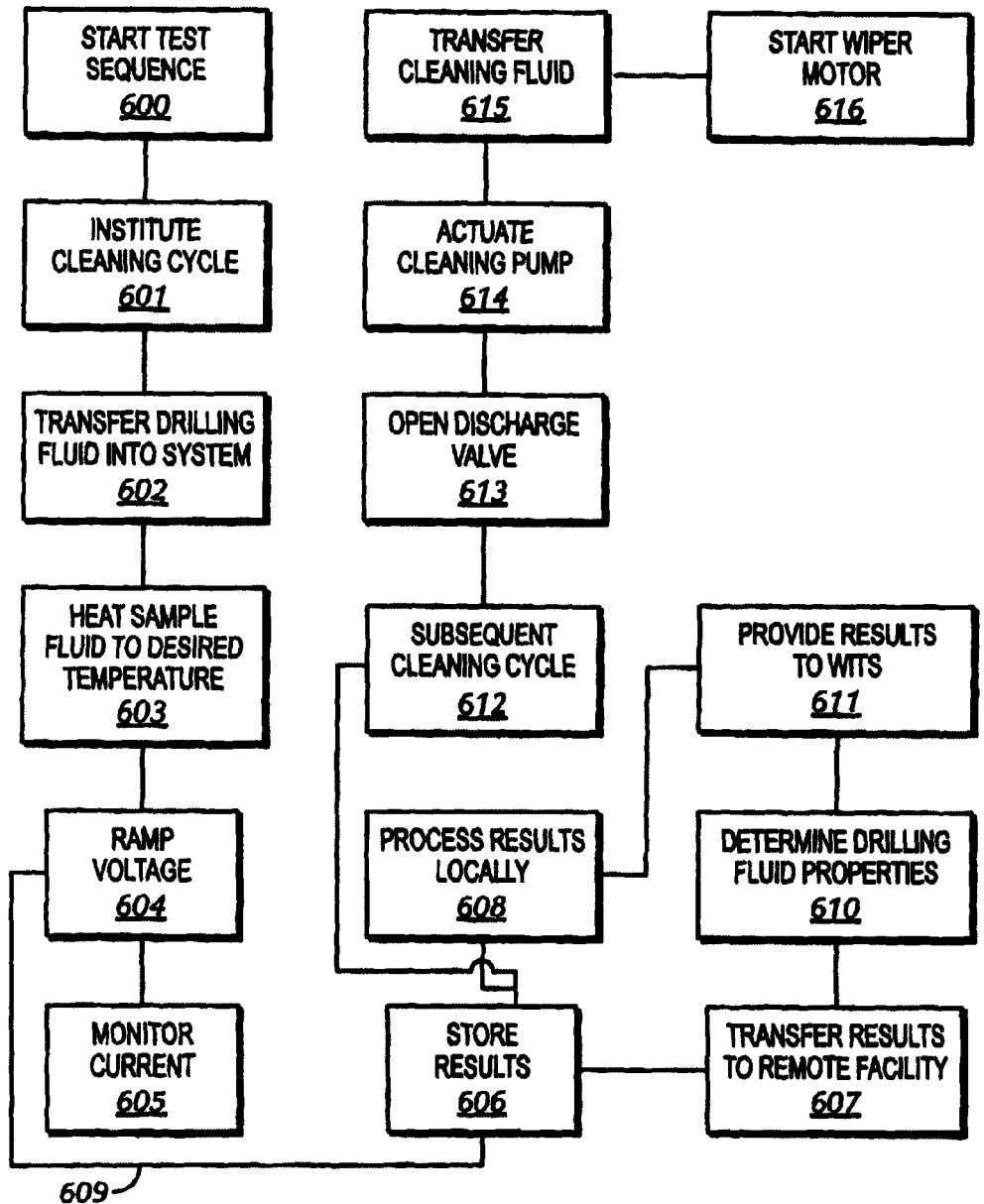
FIG. 22 is a flow chart of a process for analyzing drilling fluids according to embodiments of the present disclosure.

Referring to FIG. 22, a flow chart of an exemplary operations sequence according to methods of the present disclosure is shown. During a typical testing cycle an operation may select a start option 600 to initiate a testing sequence. Before actual testing begins, the probe may be cleaned by instituting a cleaning cycle 601, ensuring that any residual fluid that may have adhered to the probe is removed. After the device is cleaned, drilling fluid is transferred 602 from an active drilling fluid system through the inlet as cleaning fluid is removed from the device. The sample fluid is then heated 603 to a particular temperature, for example between 50° C. and 150° C. When the desired temperature has been achieved, the voltage is ramped up 604 at a rate of about 150V/s at 340 Hz. The current is then monitored 605 until 61 microamps are detected or 2000V are provided. The results are stored 606 for later transference to a remote facility for processing 607 or other use for local processing 608. The steps of ramping the voltage 504, monitoring 605, and storing the results 606 are subsequently repeated 609 until the desired number of tests have been completed.

Various additional steps may be added in specific applications, thereby allowing the device to collect additional data. For example, in certain operations, the chamber of the device may be pressurized, thereby decreasing the amount of heat required to increase the temperature. In certain operations, the pressure may be increased within a range of 4-6 bar.

During testing, a single fluid sample may be tested multiple times, at different temperatures. The multiple tests may be used to remove outliers that may otherwise skew the results. Additionally, in gel strength tests, a single fluid may be tested at various temperatures and at different rotational speeds. For example, the sleeve or cup of the viscometer may be rotated at 3, 6, 300, and 600 RPMs, thereby allowing the gel strength to be determined.

After the data is collected and stored 606, one or more drilling fluid properties, such as viscosity, gel strength, and/or electric stability are determined 610. The determined results may then be displayed directly on the device or otherwise displayed through a web server. In certain embodiments, the results may also be provided 611 to the Wellsite Information Transfer specification ("WITS") as a specific user-defined record. After all tests on a specific fluid are performed, a subsequent cleaning cycle may be initiated 612. In the subsequent cleaning cycle, the discharge valve is opened 613, the cleaning fluid pump actuated 614, and cleaning fluid is transferred 615 into the device. The wiper motor is then started 616, thereby cleaning the surfaces of the device, probe, viscometer, etc. The device is then in condition to test a subsequent fluid sample.

Figure 23:
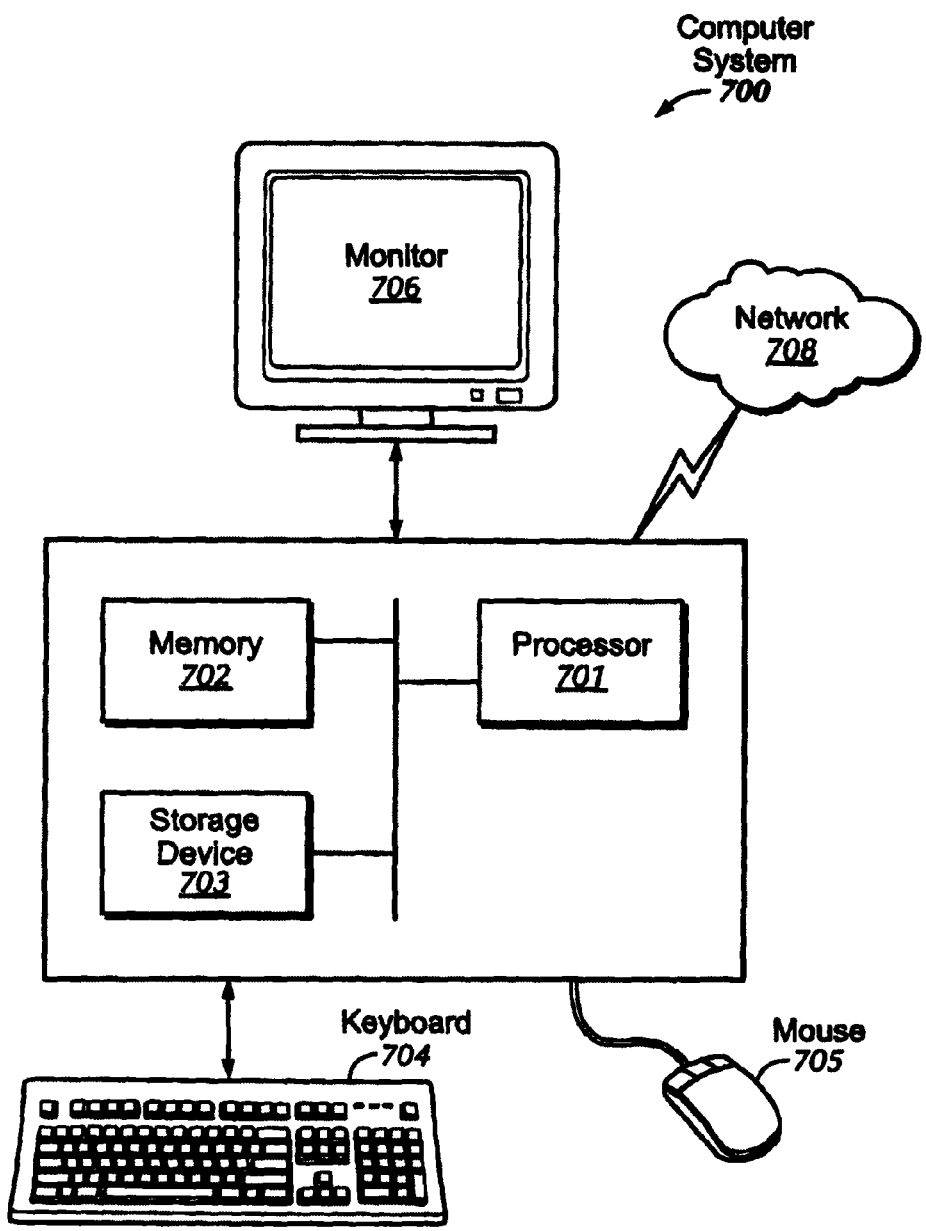
FIG. 23 is a schematic representation of a computer system according to embodiments of the present disclosure.

Embodiments of the present disclosure may be implemented on virtually any type of computer regardless of the platform being used. For example, as shown in FIG. 23, a computer system 700 includes one or more processor(s) 701, associated memory 702 (e.g., random access memory (RAM), cache memory, flash memory, etc.), a storage device 703 (e.g., a hard disk, an optical drive such as a compact disk drive or digital video disk (DVD) drive, a flash memory stick, etc.), and numerous other elements and functionalities typical of today's computers (not shown). In one or more embodiments of the present disclosure, the processor 701 is hardware. For example, the processor may be an integrated circuit. The computer system 700 may also include input means, such as a keyboard 704, a mouse 705, or a microphone (not shown). Further, the computer system 700 may include output means, such as a monitor 706 (e.g., a liquid crystal display (LCD), a plasma display, or cathode ray tube (CRT) monitor). The computer system 700 may be connected to a network 708 (e.g., a local area network (LAN), a wide area network (WAN) such as the Internet, or any other type of network) via a network interface connection (not shown). Those skilled in the art will appreciate that many different types of computer systems exist, and the aforementioned input and output means may take other forms. Generally speaking, the computer system 700 includes at least the minimal processing, input, and/or output means necessary to practice embodiments of the present disclosure.

Further, those skilled in the art will appreciate that one or more elements of the aforementioned computer system 700 may be located at a remote location and connected to the other elements over a network. Further, embodiments of the present disclosure may be implemented on a distributed system having a plurality of nodes, where each portion of the present disclosure (e.g., the local unit at the rig location or a remote control facility) may be located on a different node within the distributed system. In one embodiment of the invention, the node corresponds to a computer system. Alternatively, the node may correspond to a processor with associated physical memory. The node may alternatively correspond to a processor or micro-core of a processor with shared memory and/or resources. Further, software instructions in the form of computer readable program code to perform embodiments of the invention may be stored, temporarily or permanently, on a computer readable medium, such as a compact disc (CD), a diskette, a tape, memory, or any other computer readable storage device.

The computing device includes a processor 701 for executing applications and software instructions configured to perform various functionalities, and memory 702 for storing software instructions and application data. Software instructions to perform embodiments of the invention may be stored on any tangible computer readable medium such as a compact disc (CD), a diskette, a tape, a memory stick such as a jump drive or a flash memory drive, or any other computer or machine readable storage device that can be read and executed by the processor 701 of the computing device. The memory 702 may be flash memory, a hard disk drive (HDD), persistent storage, random access memory (RAM), read-only memory (ROM), any other type of suitable storage space, or any combination thereof.

The computer system 700 is typically associated with a user/operator using the computer system 700. For example, the user may be an individual, a company, an organization, a group of individuals, or another computing device. In one or more embodiments of the invention, the user is a drill engineer that uses the computer system 700 to remotely access a fluid analyzer located at a drilling rig.

Advantageously, embodiments disclosed herein may provide an automated system for determining an electric stability, viscosity, and/or gel strength of a fluid, such as a drilling or completion fluid. The automated system may be capable of being controlled from a remote location, as well as executing various sampling and testing protocols, so as to allow the system to run without significant manual oversight. The system may also provide for more robust and accurate analysis, as a single sample of fluid may be tested multiple times thereby allowing the system or operator to remove outliers and/or false readings.

Also advantageously, the system may be a closed system, thereby allowing the pressure to be controlled. Control of the pressure may thereby also the boiling point of a sample to be adjusted, so that the temperature required during the testing may be decreased. The closed system may also provide for more accurate measurements, and the pressure can be readily controlled, modulated, and monitored. Accordingly, pressure or temperature sensitive measuring devices or components may be less likely to be affected during routine operation.

Advantageously, embodiments of the present disclosure having a magnetic coupling may provide more accurate results due to reduced seal drag. Also, as the viscosity, electrical stability, and gel strength tests may be performed simultaneously, the time required to determine the respective drilling fluid properties may be reduced. Because the data may be transmitted and properties determined in real-time, the drilling fluids at the rig may be adjusted as required, thereby decreasing the overall cost of drilling, as well as potentially decreasing the likelihood of rig damaging events, such as blowouts.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. An automated electrical stability meter for measuring electrical stability of a sample of fluid, the meter comprising:
   a housing having an inlet and an outlet;
   at least one actuated valve disposed proximate the inlet and configured to open and close to provide a sample of fluid into the housing;
   an electronic control module configured to send a signal to the at least one valve;
   a probe assembly operatively coupled to the electronic control module, the probe assembly comprising:
      an electrode probe having two electrodes and a probe gap therebetween;
   a disc coupled to a rotatable shaft and positioned between the probe gap; and
   an agitator coupled to the rotatable shaft a distance apart from the disc, the agitator comprising one or more blades.

2. The automated electrical stability meter of claim 1, further comprising at least one of as thermal jacket and a cooling loop disposed around the housing.

3. The automated electrical stability meter of claim 1, further comprising a pump configured to pump the fluid in and out of the housing.

4. The automated electrical stability meter of claim 1, further comprising a temperature sensor disposed in the housing.

5. The automated electrical stability meter of claim 1, wherein the housing is pressurized to a pressure ranging between 4 and 6 bar.

6. The automated electrical stability meter of claim 1, further comprising:
   at least one cheek valve.

7. The automated electrical stability meter of claim 1, further comprising:
   a viscometer sleeve disposed in the housing;
   a bob disposed in the viscometer sleeve, wherein an annulus is formed between the viscometer sleeve and the bob, and wherein at least one of the viscometer sleeve and the bob is configured to rotate,
   a motor operatively coupled to at least one of the viscometer sleeve and the bob; and
   a torque measuring device operatively coupled to the viscometer sleeve and the bob.

8. The automated electrical stability meter of claim 1, further comprising:
   a test chamber, the test chamber comprising:
      an injection port in fluid communication with the inlet;
      a slide disposed within the test chamber, the slide comprising a sample cavity; and
      a test port;
   an x-ray fluorescence spectrometer disposed within a second housing; and
   at least one motor operatively coupled to the slide of the test chamber.

9. The automated electrical stability meter of claim 8, further comprising:
   a viscometer sleeve disposed in the housing;
   a viscometer bob disposed in the sleeve, wherein an annulus is formed between the viscometer sleeve and the bob, and wherein at least one of the viscometer sleeve and the bob is configured to rotate,
   a motor operatively coupled to at least one of the viscometer sleeve and the bob; and
   a torque measuring device operatively coupled to the viscometer sleeve and the bob.

10. An automated viscometer comprising:
    a housing having an inlet and an outlet;
    a viscometer sleeve disposed in the housing;
    a bob disposed in the sleeve, wherein an annulus is formed between the viscometer sleeve and the bob, and wherein at least one of the viscometer sleeve and the bob is configured to rotate,
    a motor operatively coupled to at least one of the viscometer sleeve and the bob;
    a torque measuring device operatively coupled to the viscometer sleeve and the bob;
    a test chamber, the test chamber comprising:
       an injection port in fluid communication with the inlet;
       a slide disposed within the test chamber, the slide comprising a sample cavity; and
       a test port;
    an x-ray fluorescence spectrometer disposed within a second housing; and
    at least one slide motor operatively coupled to the slide of the test chamber, the slide being movable between a fill position, where the sample cavity is in alignment with the injection port, and a test position, where the sample cavity is in alignment with the test port.

11. The automated viscometer of claim 10, further comprising a magnetic coupling disposed between the bob and the torque measuring device.

12. The automated viscometer of claim 10, further comprising a pump configured to pump a fluid in and out of the housing.

13. The automated viscometer of claim 10, further comprising an agitator disposed in the housing, wherein the agitator is operatively coupled to a motor.

14. The automated viscometer of claim 10, further comprising at least one actuated valve disposed proximate the inlet and at least one actuated valve disposed proximate the outlet, the actuated valves configured to open and close to provide a sample of a fluid into and out of the housing.

15. The automated viscometer of claim 14, further comprising at least one check valve.

* * * * *